US012256912B2

United States Patent
Karasic et al.

(10) Patent No.: US 12,256,912 B2
(45) Date of Patent: Mar. 25, 2025

(54) TENDON HARVESTING ASSEMBLIES AND METHODS

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Geoffrey Ian Karasic, Raynham, MA (US); Ali Hosseini, Quincy, MA (US); Christopher David MacCready, Medfield, MA (US); Chun Liu, Brookline, MA (US); James Hunt, Hanover, MA (US); Matthew Edwin Koski, Westford, MA (US); Paul McGovern, Hanson, MA (US); Jacob Peabody, Londonderry, NH (US)

(73) Assignees: Smith & Nephew, Inc., Memphis, TN (US); Smith & Nephew Orthopaedics AG, Zug (CH); Smith & Nepew Asia Pacific Pte. Limited, Singapore (SG)

( * ) Notice: Subject to any disclaimer, the term of this patent is extended or adjusted under 35 U.S.C. 154(b) by 507 days.

(21) Appl. No.: 17/769,805

(22) PCT Filed: Oct. 16, 2020

(86) PCT No.: PCT/US2020/056085
§ 371 (c)(1),
(2) Date: Apr. 18, 2022

(87) PCT Pub. No.: WO2021/076968
PCT Pub. Date: Apr. 22, 2021

(65) Prior Publication Data
US 2022/0409192 A1 Dec. 29, 2022

Related U.S. Application Data

(60) Provisional application No. 63/036,554, filed on Jun. 9, 2020, provisional application No. 62/949,611, filed
(Continued)

(51) Int. Cl.
A61B 17/32 (2006.01)
A61B 17/00 (2006.01)
A61B 90/00 (2016.01)

(52) U.S. Cl.
CPC ........... *A61B 17/00008* (2013.01); *A61B 2017/00738* (2013.01); *A61B 2017/00969* (2013.01);
(Continued)

(58) Field of Classification Search
CPC .... A61B 17/00008; A61B 2017/00969; A61B 17/320016; A61B 2017/00778; A61F 2/08
See application file for complete search history.

(56) References Cited

U.S. PATENT DOCUMENTS 5,667,480 A * 9/1997 Knight ............ A61B 17/00234
606/190
5,681,314 A 10/1997 Derquin et al.
(Continued)

FOREIGN PATENT DOCUMENTS

DE 102011109715 2/2013

OTHER PUBLICATIONS

Search Report and Written Opinion for PCT/US2020/056085 filed Oct. 16, 2020, Feb. 2, 2021, 18 pages.

*Primary Examiner* — Katherine H Schwiker
(74) *Attorney, Agent, or Firm* — Norman F. Hainer, Jr.; Kate Ryland Tetzlaff

(57) ABSTRACT

A harvesting assembly for harvesting a tissue graft from surrounding tissue is disclosed including a guide. The guide includes a means for fixedly engaging with an anterior surface of the tendon. The guide also includes a means of guiding a cutting blade along a preferred trajectory into and along a length of the tendon. The guide also includes a means of guiding a truncating blade along a preferred trajectory across a width of tendon. The cutting blade may include two parallel blades for forming lateral sides of the tendon graft simultaneously. Each of the two parallel blades
(Continued)

may define a leading edge that extends along at least a 90 degree arc that is equidistant from a stop on the cutting blade. The stop in combination with the guide may limit a cut depth into the tendon for a range of cutting blade handle elevation angles.

12 Claims, 20 Drawing Sheets

Related U.S. Application Data on Dec. 18, 2019, provisional application No. 62/944,452, filed on Dec. 6, 2019, provisional application No. 62/916,304, filed on Oct. 17, 2019.

(52) U.S. Cl.
CPC ............ *A61B 2017/320052* (2013.01); *A61B 2017/320064* (2013.01); *A61B 2090/034* (2016.02)

(56) References Cited

U.S. PATENT DOCUMENTS

| | | |
|---|---|---|
| 5,733,289 A | 3/1998 | Seedhom |
| 2015/0057693 A1 | 2/2015 | Burroughs, III |
| 2017/0135716 A1 | 5/2017 | Endo |
| 2017/0245845 A1* | 8/2017 | Fujii ................. A61B 18/1482 |

* cited by examiner

TENDON HARVESTING ASSEMBLIES AND METHODS

CROSS-REFERENCE TO RELATED APPLICATIONS

This application is a U.S. National Phase Entry of PCT Application Serial No. PCT/US2020/056085 filed Oct. 16, 2020 and titled "TENDON HARVESTING ASSEMBLIES AND METHODS", which claims the benefit of U.S. Provisional App. No. 62/916,304 filed Oct. 17, 2019 titled "Surgical Cutting Assembly and Methods of Use Thereof" and U.S. Provisional App. No. 62/944,452 filed Dec. 6 5, 2019 and titled "Tendon Amputating Device" and U.S. Provisional App. No. 62/949,611 filed Dec. 18, 2019 and titled "Quadriceps Tendon Graft Harvester" and U.S. Provisional App. No. 63/036,554 filed Jun. 9, 2020 titled "Tendon Truncation Device and Method"; all herein incorporated by reference in their entirety.

FIELD

The present disclosure relates to surgical cutting assemblies and more particularly, to surgical cutting assemblies for harvesting a portion of tendon tissue from itself.

BACKGROUND

The quadriceps tendon is often used as a source of tissue graft for ligament surgery, such as anterior cruciate ligament (ACL) reconstruction. However, graft harvesting from the quadriceps tendon presents several challenges, as the quadriceps tendon is typically larger and stronger than other tendons, and also stiffer and less prone to stretching or deformation. Existing devices for harvesting the quadriceps tendon can require multiple cuts to harvest a graft. Existing devices can be deviated from their intended cutting path by the tougher tendon tissue, rendering an uneven graft strip cross section that may be useless. Furthermore, harvesting the tissue graft with a free-hand (for example, with a scalpel blade) is time-consuming and results in difficulty of graft reproducibility. Accessing the end of the tendon strip to terminate or amputate the graft tissue, requires either a larger skin incision for access or alternatively may be performed somewhat blind, and therefore time-consuming and risks inadvertent tissue damage. Therefore, it is desirable to have an improved device or system that can reliably and reproducibly remove a strip or portion of tendon tissue from the remaining tendon.

SUMMARY

Described herein is a surgical cutting assembly or devices for harvesting a tissue graft from surrounding tissue, such as a quadriceps tendon. Defining the entire quadriceps tendon as a single first tissue, the assemblies devices and methods described herein are configured to disconnect a portion or strip of this first tissue from itself. Before being harvested or disconnected, this portion or strip is continuous with and non-discernable from the first tissue. Stated otherwise, the portion or strip disconnected by the herein disclosed assemblies or devices is provided continuously coupled to the first tissue, along the entire length of the resultant strip or portions, the entire length including at least three cut surfaces. The assemblies and devices that form the strip continuously cut through the single first tissue along the entire length of the resulting strip or portion. The shape of the resultant portion or strip is defined by the assembly or devices herein and can be altered with differing dimensions and methods of use of the disclosed systems, assemblies and cutting tools. Contrary to this a vessel harvesting tool for example, disconnects a target vessel from surrounding connective tissue that may include smaller vessels, and other connective and fatty tissues that are not vessels. It follows therefore, that this example harvested strip of tissue (the target vessel) is disconnected from a plurality of tissues that are different from the target vessel; the target vessel is not a removed portion of itself along its entire length. The target vessel is discernable from the connective tissue around it. It is coupled along its length to a plurality of tissues, and these tissues are different in composition to the target vessel. In addition, the vessel at least partially defines the shape and size of the harvesting tool. As a further example, a polyp removal device disconnects a polyp from a substrate tissue, the polyp and substrate tissue not being the same tissue, and the polyp only coupled to the substrate at a first end of the polyp. In addition, the polyp is discernable from the substrate tissue and a device that disconnects a polyp does not define the size of polyp removed. All of the polyp is removed.

Turning now to this disclosure, an example method of use of a guide assembly is disclosed. The guide of the assembly is placed on a surface of the tissue from which the graft is to be removed. The assembly also includes a device with a three-sided blade, attached via a hinge to a handle. Handle allows the user to push the device through the guide along internal tracks within the guide. Upon being pushed through the guide, the blade may simultaneously make two longitudinal cuts and one posterior cut along the tendon. Once the blade reaches the end of the guide, the geometry of the guide forces the blade to rotate to make a final, transverse cut, thus separating the tendon graft from surrounding tissue. The cutting assembly of this disclosure advantageously provides a method of creating tissue grafts with increased graft reproducibility and dimensional precision, as well as decreased procedure time, compared to both current cutting devices and to free-hand methods.

In further embodiments, a surgical cutting assembly of this disclosure includes a guide having an elongated body including a proximal end, a distal end and a cannulation defined by opposing sidewalls of the guide extending along a longitudinal axis. An inner surface of the opposing sidewalls defines a track. The assembly also includes a blade having a handle end and a cutting end coupled to a distal end of the handle. The cutting end is configured to be axially moveable along the track and pivotable with respect to the handle from a first position to a second position. In the first position, the cutting end is configured to extend from a lower surface of the guide to make at least one cut in soft tissue along the longitudinal axis. In moving towards the second position, the cutting end is configured to pivot with respect to the handle to make another cut in the soft tissue transverse to the longitudinal axis.

In further examples, the soft tissue is a quadriceps tendon. In examples, an upper surface of the guide defines a window for direct visualization of the movement of the blade along the track. In examples, at least one of the guide and the blade include markings for indicating a desired length of a tissue graft. In examples, the track includes a first recess and a second recess, and a bar extending between the first and second recesses. In examples, an outer surface of the blade includes a first pin configured for engaging the first recess. The first pin is both slidable and rotatable within the first recess. In examples, an outer surface of the blade includes a second pin configured for engaging the second recess, the second pin being slidable but not rotatable within the second recess. In examples, the first pin is substantially cylindrical in shape, and the second pin is substantially square in shape. In examples, the cutting end includes two stripping edges for forming the at least one cut along the longitudinal axis, a cutting edge extending between the two stripping edges for forming the at least one cut transverse to the longitudinal axis, and an opening defined between the stripping edges and the cutting edge. In examples, the guide includes an arcuate projection extending from an upper surface of the guide into the cannulation. In the second position, the arcuate projection is received within the opening of the cutting end. In examples, the guide is made of plastic. In examples, at least one of the handle and the blade is made of metal.

In some example embodiments, a surgical cutting assembly for harvesting a portion of tendon tissue and thereby forming a graft is disclosed. The assembly includes a guide with an elongated body having a proximal end, a distal end and a cannulation defined by opposing sidewalls of the guide extending along a longitudinal axis. An inner surface of the opposing sidewalls defines a track. The assembly also includes a blade having a handle end and a cutting end coupled to a distal end thereof, the cutting end configured to operatively couple to the guide track such that axial movement of the handle axially moves the cutting end along the track for a first length and rotates the cutting end for a second length; rotating is with respect to the handle from a first position to a second position. In the first position, the cutting end is configured to extend from a lower surface of the guide to make at least one cut in the tendon tissue along the longitudinal axis. In rotating to the second position, the cutting end is configured to cut the tendon tissue at an angle to the longitudinal axis.

In some example embodiments, the cutting end is configured to cut three sides of the tendon tissue simultaneously. These three sides of the tendon tissue may include two lateral sides of the graft, spaced apart and thereby defining a width of the graft. Moving the cutting end from the first position to the second position may simultaneously form two lateral surfaces of the graft and also separate a graft end from the tendon tissue. The track may include a first recess and a second recess, and a bar extending between the first and second recesses and an outer surface of the blade may include a first pin configured for engaging the first recess, the first pin being both slidable and rotatable within the first recess. An outer surface of the blade may include a second pin configured for engaging the second recess, the second pin being slidable but not rotatable within the second recess. The first pin may be substantially cylindrical in shape, and the second pin may be substantially square in shape. The cutting end may include two lateral edges for forming the two lateral cuts along the longitudinal axis, a cutting edge extending between the two lateral edges for forming the at least one cut transverse to the longitudinal axis, and an opening defined between the two lateral edges and the cutting edge. The guide may include an arcuate projection extending from an upper surface of the guide into the cannulation and wherein, in the second position, the arcuate projection is received within the opening of the cutting end. The guide may include an arcuate projection that terminates with a stabilizing surface configured to engage and stabilize the tendon tissue while the cutting end moves from the first position to the second position, the arcuate projection disposed within the opening of the cutting end in the second position.

In examples, methods of tissue harvesting of this disclosure include placing a lower surface of a guide against soft tissue. The guide has an elongated body including a proximal end, a distal end and a cannulation defined by opposing sidewalls of the guide extending along a longitudinal axis. An inner surface of the opposing sidewalls defines a track. A blade is inserted into the cannulation of the guide. The blade has a handle and a cutting end coupled to a distal end of the handle. The cutting end is configured to be axially moveable along the track and pivotable with respect to the handle from a first position to a second position. The cutting end is moved in the first position along the track to make at least one cut in the soft tissue along the longitudinal axis. The cutting end is then pivoted with respect to the handle to make another cut in the soft tissue transverse to the longitudinal axis.

Various embodiments are directed to a Quadriceps Tendon Harvesting System for use in procedures, such as arthroscopic procedures. For example, a tendon harvesting system for forming a tendon graft from a tendon is disclosed including a guide. The guide defines a first end and a second end and a length therebetween. A first leg extends from the guide first end and a second leg extends from the guide second end. The first and second legs both define lengths that elevate the guide above and spaced away from the target tissue. In some embodiments the guide length may be adjustable. In some embodiments the first and second legs each have free ends that include tissue engaging teeth. In some embodiments the first leg comprises a first pair of legs spaced apart a first distance to receive a tendon harvester therebetween, the first distance may be configured to limit the trajectory of the tendon harvester as the tendon harvester moves along the tendon. The first pair of legs may have a length such that the tendon harvester may extend therebetween at a range of elevation angles relative to a guide longitudinal axis. In some embodiments the range of elevation angles may range between 0-80 degrees relative to the guide longitudinal axis. In some embodiments a tendon harvester may include two parallel blades at a distal end for forming lateral sides of the tendon graft simultaneously. Each of the two parallel blades may define a leading edge that extends along at least a 90 degree arc, the leading edge equidistant from a stop on the tendon harvester such that a depth of cut into the tendon is limited by the stop for a range of harvester elevation angles. In some embodiments the range of elevation angles is between 0-80 degrees relative to the guide longitudinal axis. In some embodiments the second leg is configured to receive an amputating blade therealong and control a trajectory of the amputating blade, the second leg further comprising means to limit penetration of a leading edge of the amputating blade into the tendon. In some embodiments the second leg is configured to limit a trajectory of a tendon harvester along the tendon.

A method of harvesting a graft from a tendon is also disclosed including adjusting a harvesting guide length and placing a first leg of the harvesting guide at a first end of a tendon, a second end of the harvesting guide at a second end of the tendon so as to place a guide bridge disposed between the first and second leg along and elevated above the tendon. A tendon harvester is then placed at an angle relative to the guide bridge and below the guide bridge and translated to form two lateral sides of the graft. The trajectory of the tendon harvester may be limited by the guide first leg and a length of the trajectory may be limited by the second leg. The method may further include orienting the tendon harvester at a range of angles relative to a longitudinal axis of the guide bridge, ranging from 0-80 degrees. The method may further include engaging teeth at free ends of the first and second legs with the tendon to limit unintended movement of the guide. The first leg may comprises a first pair of legs spaced apart a first distance, and the method may also include extending the harvester between the first pair of legs and translating the harvester along the trajectory plane controlled by the first pair of legs. The method may further include orienting the harvester initially at an elevation angle relative to the guide longitudinal axis and gradually reducing the elevation angle while translating the harvester along the trajectory. The method may alternatively include orienting the harvester initially at an elevation angle relative to the guide longitudinal axis and gradually decreasing the elevation angle while translating the harvester along the trajectory such as towards the patient knee. The tendon harvester may include two parallel blades, each blade having a leading edge that extends along an arc that is equidistant from a stop on the tendon harvester such that while translating the harvester a depth of cut into the tendon is limited by the stop for a range of elevation angles of the tendon harvester relative to the tendon tissue, while providing constant cutting depth. The range of elevation angles may be between 0-80 degrees. The method may further include sliding an amputation blade along a path defined by the second leg and terminating the graft. The method may further include sliding the amputation blade up to a stop associated with the second leg for limiting depth of a leading edge of the amputating blade beyond the second leg and thereby a depth of cut of the amputating blade into the tendon.

Various embodiments are directed to a Quadriceps Tendon Amputation Device for use in procedures, such as arthroscopic procedures. More particularly, example embodiments are directed to a surgical instrument for amputating an end of a tendon strip from a tendon, the instrument having a hook for at least partially wrapping around and sliding along the pre-formed tendon strip, and a blade that may axially slide to transect the tendon strip. The hook is configured to receive the blade therein to cover or shield at least a portion of the blade, when the blade has transected the tendon.

In some embodiments, a tendon amputating device is disclosed including an outer housing and cutting tool having a sharp leading edge operatively coupled to the outer housing and axially slideable relative to the housing. The device also includes a retention hook at a distal end of the device defining an opening. The cutting tool is axially slideable between a retracted configuration wherein a sharp leading edge of the cutting tool is shielded by the housing and a cut configuration, wherein the sharp leading edge is partially shielded by the retention hook and the tendon strip is transected. The retention hook has a lateral opening configured to receive a tendon strip therethrough, the lateral opening may be closed by the housing. In some embodiments the tendon amputating device may also include a clamp operatively coupled to the housing and axially slideable so as to clamp the tendon strip between the retention hook and clamp. In some embodiments the clamp may be disposed within the outer housing. In some embodiments the retention hook defines a distal end of the outer housing. In some embodiments the housing is axially slideable relative to the retention hook to clamp the tendon strip between the retention hook and a leading edge of the housing. In some embodiments the housing and retention hook further comprise mating ratcheting constructs to limit axial sliding of the retention hook relative to the housing.

A method of amputating a preformed tendon strip is also disclosed including positioning a tendon strip cross section through a lateral opening at a distal end of an amputation device and into a cavity of the amputating device. The method further includes axially sliding a clamp portion of the amputating device across the lateral opening to encircle the tendon strip cross section disposed within the cavity and then advancing the amputation device encircling the tendon strip along the tendon strip towards an attached end of the tendon strip. The method further includes axially sliding a cutting tool across the cavity of the amputation device and into a distal portion of the amputation device so that a leading sharp edge of the cutting tool is covered by the device distal portion and the tendon strip cross section in transected. The method may further include advancing the clamp further to more tightly clamp the tendon strip before axially sliding the cutting tool.

Another method of amputating a preformed tendon strip is also disclosed including placing a tendon strip cross section through a lateral opening of an amputation device hook and axially sliding a housing of the amputating device up to a free end of the amputation device hook to close the lateral opening. This forms an aperture having a perimeter defined by the hook and housing to retain the tendon strip cross section within the aperture. The method also includes advancing the hook along the tendon strip towards an attached end of the tendon strip and axially sliding a leading sharp edge of a cutting tool across the aperture of the amputation device and into a shielded portion of the hook to transect the tendon strip cross section. The method may further include axially sliding the housing of the amputating device beyond the hook free end to more tightly clamp on the tendon strip cross section before axially sliding the cutting tool. The housing may have a planar outer surface with a series of axially spaced length markers. Advancing the hook along the tendon strip towards an attached proximal end of the tendon strip may further include stopping the advancing once a target marker of the series of axially spaced length markers is adjacent the incision. The housing may have a planar outer surface defining a constant housing width extending up to a handle end of the housing and wherein the sharp cutting edge may slide along a plane that is parallel to the planar outer surface.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

Figure 1A:
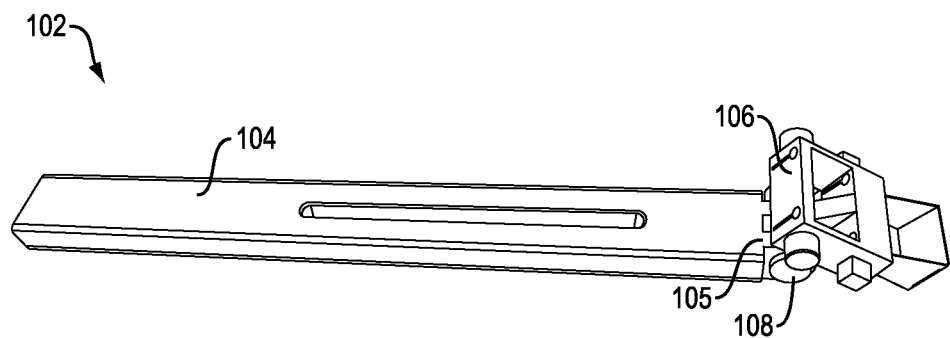
FIG. 1A illustrates an example of a cutting instrument for use with a harvesting assembly of this disclosure.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts. Use of the terms "upper," "lower," "below," and the like is intended only to help in the clear description of the present disclosure and are not intended to limit the structure, positioning and/or operation of the disclosure in any manner.

Referring now to FIG. 1A, an example of a cutting instrument 102 for use with a harvesting assembly 100 of this disclosure is shown, in perspective view. The cutting assembly 100 may be used for harvesting (that is, both stripping and amputating) a portion of a quadriceps tendon. However, it is also contemplated that the cutting assembly 100 could be used for harvesting any soft tissue or tissue graft from a larger portion both in width and length within the same tissue that is sized and cut for further use as a replacement of an injured tendon or ligament. As shown in FIG. 1A, the cutting instrument 102 generally comprises an elongated handle 104 and a blade end 106 pivotally coupled to a distal end 105 of the handle 104 by a hinge 108. In examples, the handle 104 and/or the blade end 106 can be made of a surgical grade metal, such as stainless steel or titanium.

Figure 1B:
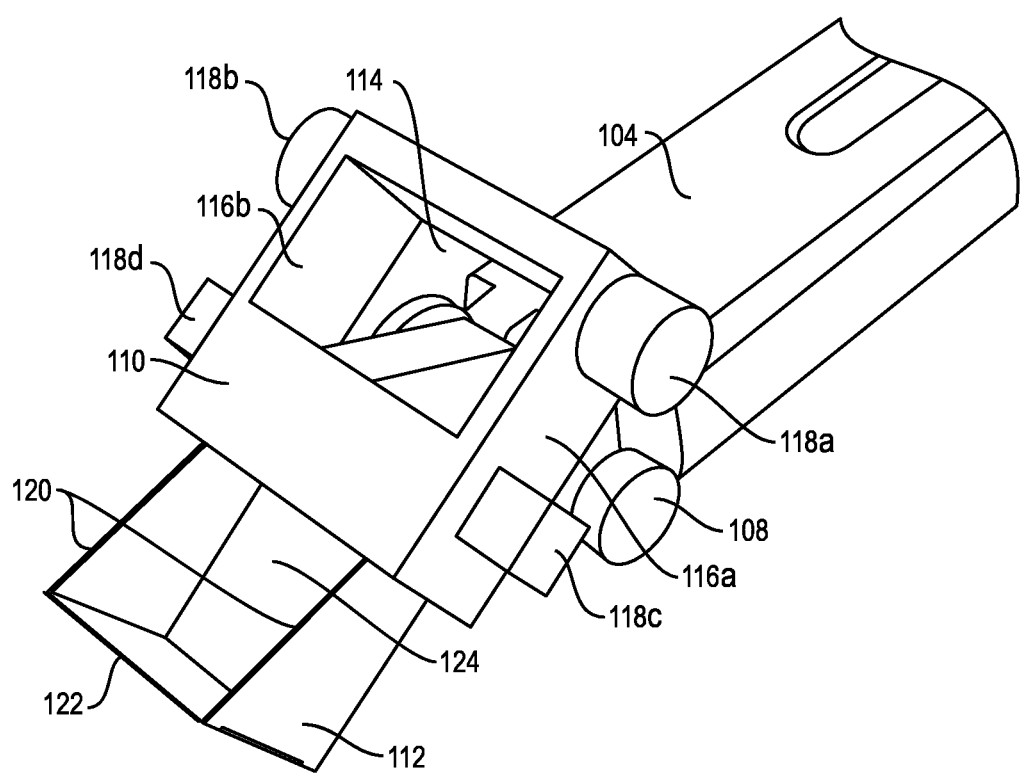
FIG. 1B is a detailed view of a distal end of the cutting instrument.

As shown in more detail in FIG. 1B, the blade end 106 comprises an upper pivot portion 110 and a lower cutting portion 112. The pivot portion 110 includes an opening 114 defined between two sidewalls 116a and 116b for receipt of a portion of the hinge 108. Two opposing upper guide pins 118a and 118b and two opposing lower guide pins 118c and 118d extend from an outer surface of the sidewalls 116a and 116b, the purpose of which will be described in more detail below. In examples, the two upper guide pins 118a and 118b are substantially cylindrical in shape, while the two lower guide pins 118c and 118d are substantially square in shape, although other shapes of the guide pins 118a-d are contemplated by this disclosure.

Still referring to FIG. 1B, the cutting portion 112 comprises two lateral cutting edges or blades 120 extending from the pivot portion 110 and a posterior cutting edge 122 extending between the two lateral cutting edges 120. The two lateral cutting edges 120 may extend parallel to each other, and may form the two lateral most surfaces of the tendon graft strip. The distance between the two lateral cutting edges 120 defines the resulting graft strip width. The posterior cutting edge 122 may extend orthogonally relative to the two lateral cutting edges 122 and may form the posterior most cut along the tendon and may therefore define a depth or thickness of the tendon strip. An opening 124 is defined between the lateral cutting edges 120, the posterior cutting edge 122, and the pivot portion 110. In examples, a distance between the lateral cutting edges 120 is selected based on the desired width of the tissue graft (for example, 10 mm). In other examples, a distance between the pivot portion 110 and the posterior cutting edge 122 is selected based on the desired depth or thickness of the tissue graft (for example, 10 mm). However, other desired widths and depths of the tissue graft are contemplated by this disclosure. All the cutting edges (120, 122) may be continuous with each other.

Figure 2A:
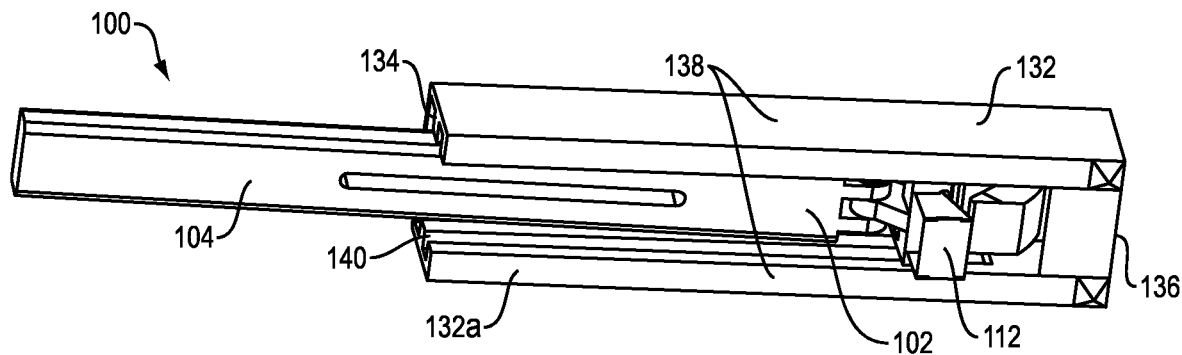
FIG. 2A is an assembled view of the harvesting assembly, in accordance with this disclosure.
Figure 2D:
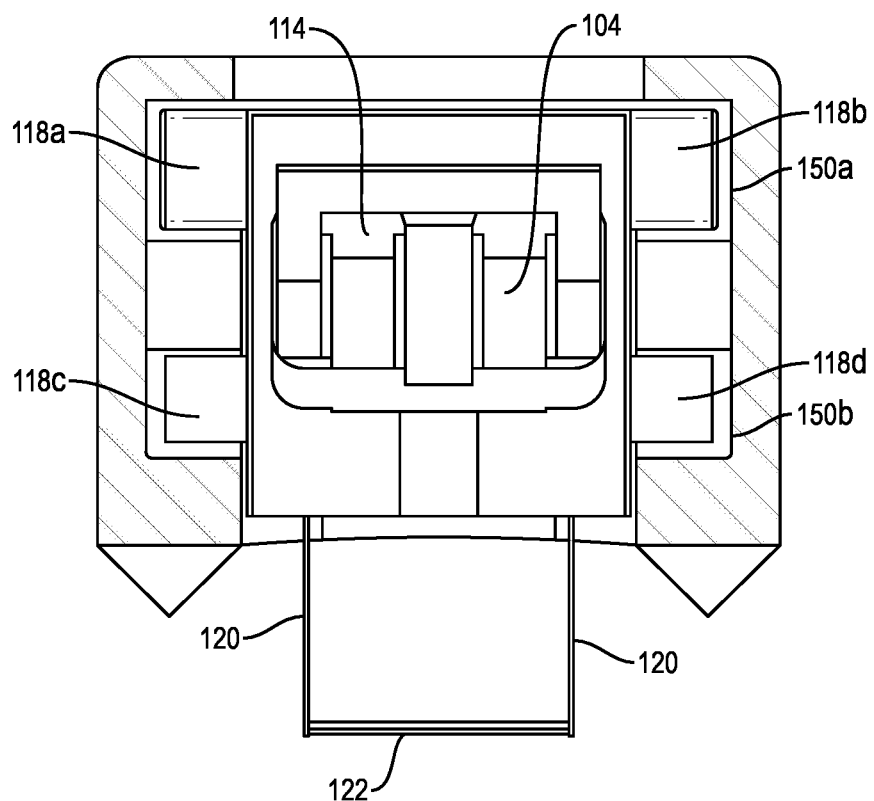
FIG. 2D is an end view of the harvesting assembly of this disclosure, with the cutting end in a stripping configuration.
Figure 2E:
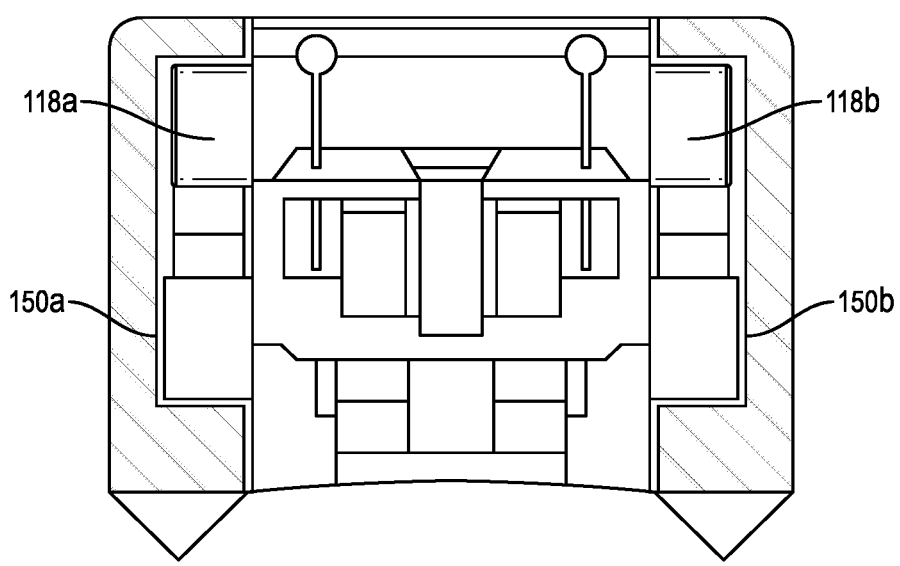
FIG. 2E is an end view of the harvesting assembly of this disclosure, with the cutting end in an amputating configuration.
Figure 3A:
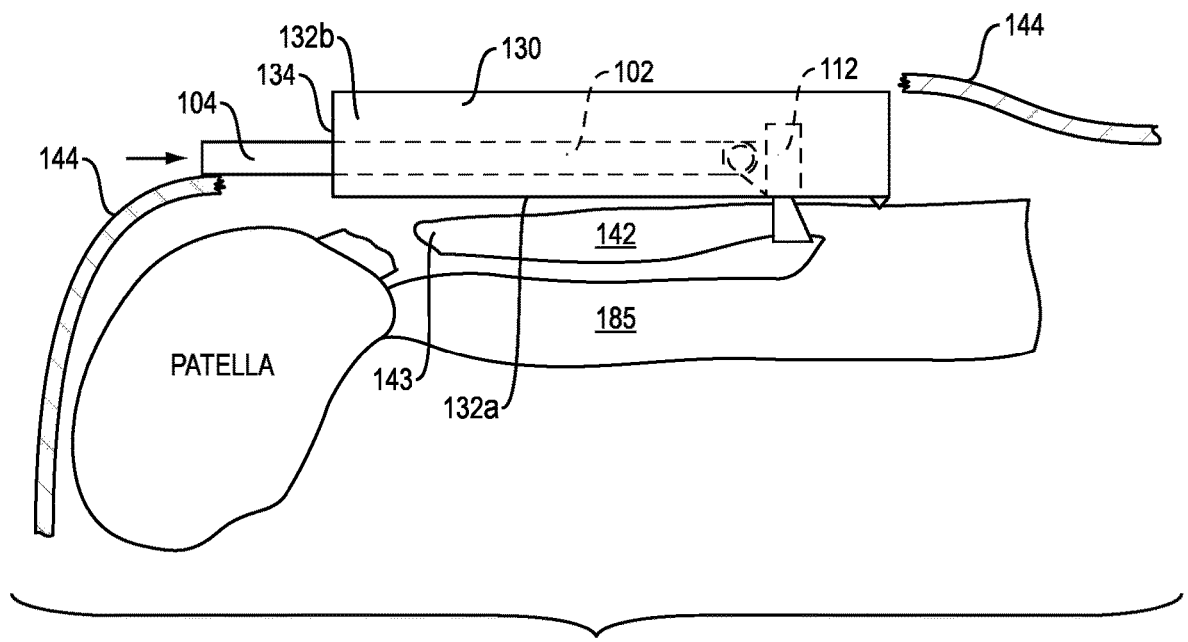
FIGS. 3A and 3B illustrate a method of using the harvesting assembly of this disclosure for harvesting a tissue graft.

Turning now to FIG. 2A, an example of the harvesting assembly 100 is illustrated including the cutting instrument 102 as described above configured for use with a cutting guide 130. In examples, the cutting guide 130 is comprised of plastic, although other suitable materials are contemplated. In examples, differently-sized cutting portions 112 may be interchangeable with the cutting guide 130 and may be removable from the cutting guide 130. The entire assembly 100 may be sterilizable (e.g., autoclavable), or may be provided as a single-use only device (i.e., disposable) or as a multiple-use device. The cutting guide 130 may comprise a generally rectangular body 132 having an open proximal end 134 and a closed distal end 136. Opposing sidewalls 138 of the body 132 define a longitudinal cannulation 140 extending from the proximal end 134 of the cutting guide 130 and open to a lower surface 132a of the body 132. The cutting guide 130 is configured to engage an anterior surface of the tendon, so to as to stabilize the tendon for reproducible cutting. A portion of the handle 104 and the blade end 106 are configured to slide through the cannulation 140 such that, in a first position, the cutting portion 112 extends below the sidewalls 138, as shown in FIG. 3A. More specifically the guide pins 118a and 118b and two opposing lower guide pins 118c and 118d are configured to ride along tracks 150a and 150b of the guide to define the path of the cutting portion 112. Thus, when the lower surface 132a of the body 132 is placed against the anterior surface of the tendon, the cutting portion 112 may extend below the anterior surface and receive the tendon graft tissue through the opening 124. This is shown in FIGS. 2D and 3A. Once the cutting portion is adjacent the distal end 136, the tracks curve and thereby rotates the cutting portion 112. This moves the cutting portion 112 anteriorly which amputates the tendon graft (separates the strip from the remainder of the tendon). A guide surface 147 is configured to provide supplemental engagement with the anterior surface of the tendon, in addition to sidewalls 138 near the distal end 136 and stabilize the graft strip while the cutting portion 112 rotates.

Figure 2C:
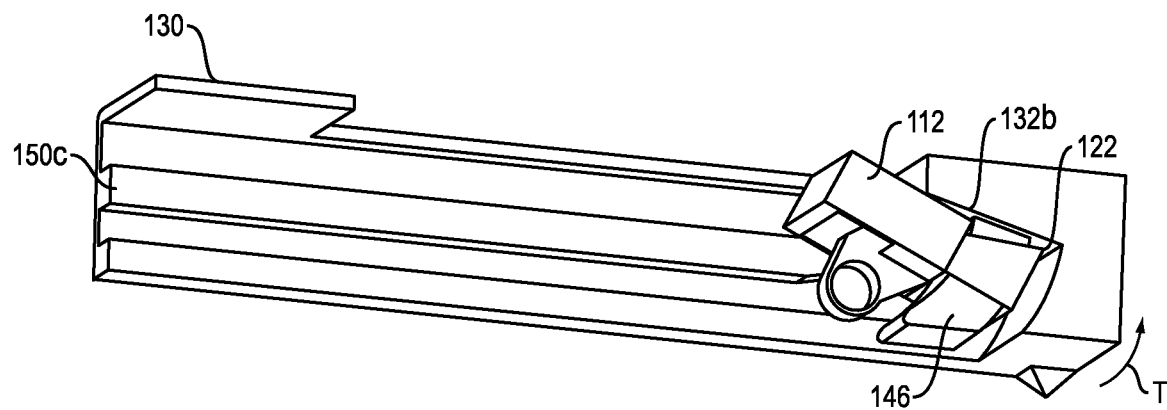
Figure 3B:
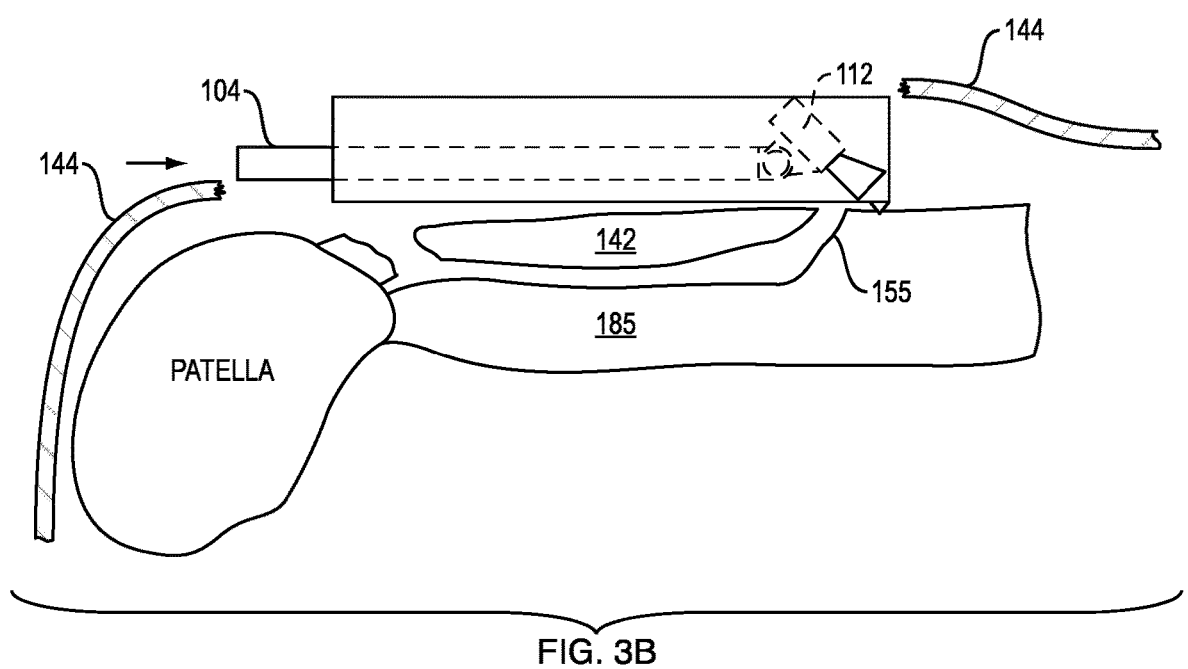

Exemplary methods of using the cutting assembly 100 of this disclosure to remove a tendon strip 142 from a tendon 185 are illustrated in at least FIGS. 3A and 3B. Initially, as shown in FIG. 3A, the lower surface 132a of the cutting guide 130 is placed substantially flush against an anterior surface of the tendon tissue 185. An opening through the skin 144 may be required to give the guide 130 access. Using the handle 104, the cutting portion 112 of the cutting instrument 102 is introduced into the proximal end 134 of the cutting guide 130. The cutting guide 130 and/or the handle 104 may comprise laser marks or other indicia for indicating a desired length of the tissue graft (for example, 7 cm). As further seen in FIG. 2C, an arcuate projection 146 extends from the upper surface 132b of the cutting guide 130 into the cannulation 140 and curves toward the proximal end 134 of the cutting guide 130. A length of the projection 146 is selected such that a lower surface 147 of the projection 146 abuts the surface of the tendon tissue 185 when the cutting guide 130 is placed on the soft tissue 142. The cutting guide 130 is placed on the tendon tissue 142 such that a distance between an end 143 of the tendon tissue 142 and the projection 146 is approximately equal to a desired length of the tissue graft.

Figure 2B:
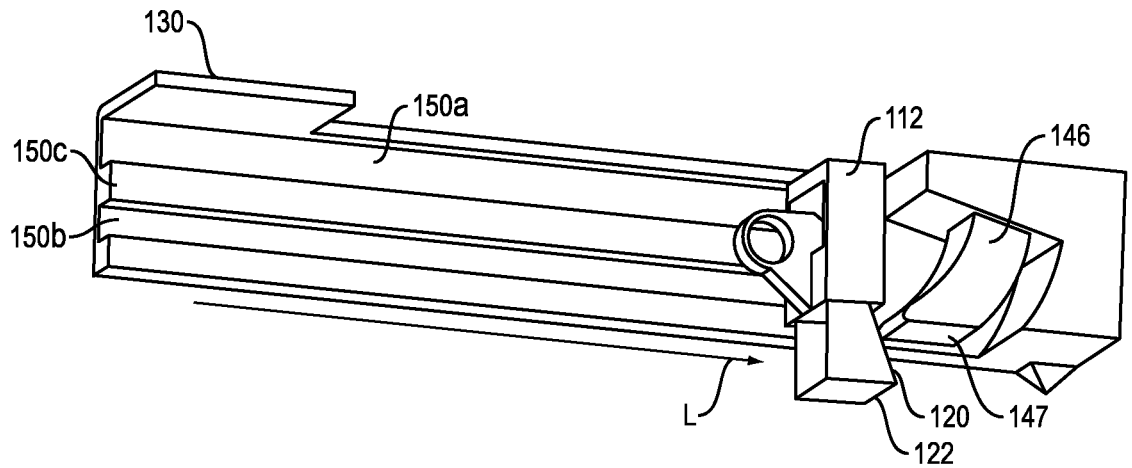
FIGS. 2B and 2C are cross sectional views of the harvesting assembly of this disclosure, in a stripping and amputating configuration respectively.
Figure 4:
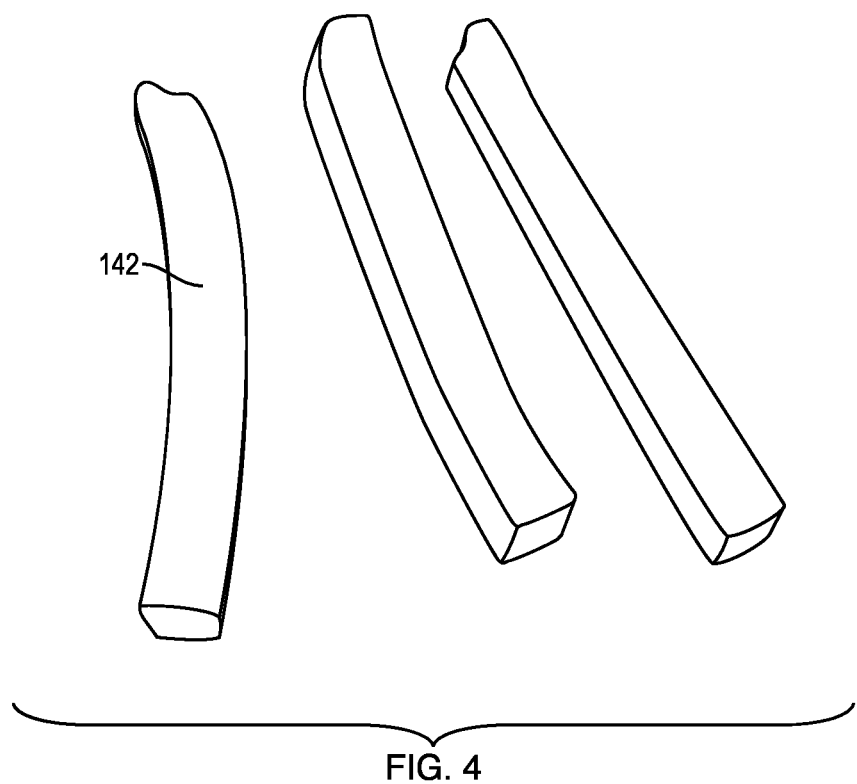
FIG. 4 shows a resulting tissue graft strip.

Turning now to FIG. 2B, a cross-section and end view of the cutting guide 130 is shown with the cutting portion 112 disposed within the cannulation 140 and the handle 104 of the cutting instrument 102 removed for ease of illustration. FIG. 2D shows an end view of the cutting guide 130 with the cutting portion 112 within the cannulation and in a position as shown in FIG. 2B. The cutting portion 112 is disposed within the cannulation 140 such that the upper guide pins 118a,b (FIGS. 1B, 2D) engage opposing upper tracks 150a extending longitudinally along an inner surface of the sidewalls 138 such that the upper guide pins 118a,b are both slidable and rotatable within the upper tracks 150a. Simultaneously, the lower guide pins 118c,d (FIG. 1B, 2D) engage opposing lower tracks 150b extending longitudinally along an inner surface of the sidewalls 138 such that the lower guide pins 118c,d are slidable but not rotatable within the lower tracks 150b. A track bar 150c extends between the upper and lower tracks 150a,b. When the handle 104 is moved distally, and with the cutting portion 112 in the first position against the soft tissue (not shown), the lateral cutting edges 120 create two longitudinal cuts L through the soft tissue. Simultaneously, the cutting edge 122 creates a posterior cut through the tendon tissue to form a generally U-shaped cut along the surface of the tendon tissue 142 (FIG. 4). As shown in FIGS. 2C and 3B, once the cutting portion 112 reaches the distal end of the cannulation 140, the force of the distal movement and the geometry of the cutting guide 130 causes the cutting portion 112 to rotate to a second position relative to a longitudinal axis of the handle 104. In the second position, the lower guide pins 118d,c move distally past the track bar 150c, allowing the cutting portion 112 to rotate on the upper guide pins 118a,b such that the projection 146 is received through the opening 124 of the cutting portion 112. At the same time, the cutting edge 122 forms a transverse cut T through the tendon tissue 185, thus forming an arcuate cut 155 at the end of the strip 142 (FIG. 3B). The cutting assembly 100 can then be removed, and the tissue graft 142 (FIG. 4) removed either manually or with another device from the surrounding tendon tissue 142.

A kit may be provided which comprises a cutting guide 130 and one or more cutting instruments 102 having differently-sized cutting portions 112 for forming differently-sized tissue grafts 152. In other examples, not shown, the stripping edges 120 of the cutting portion 112 could be substituted with supports to reduce the amount of cutting resistance against the cutting portion 112. This configuration would limit the number of cuts in the soft tissue 142 from four to two (i.e., the proximal and the distal cuts).

Elevated Tendon Harvesting System

Disclosed herein is a QT Harvesting System and a methods of use. In an example embodiment, the harvesting system includes a guide that is adjustable to accommodate differing cutting lengths in order to harvest a graft of a desired length as needed/decided by surgeon. Since the quadriceps tendon (QT) connects four muscles to patella (i.e., rectus femoris, vastus lateralis, vastus medialis, vastus intermedius), providing a trajectory before actual harvest of the graft is critical, so that the final graft has enough length required for ACL/PCL reconstruction/revision. The system disclosed may provide the surgeon with the ability to make reliable tendon graft strips without the need for a longer incision along the patient's thigh for direct visualization of the entire tendon. Typically one larger incision along almost the entire desired length of the tendon is made and either a free hand or a stripper directly on the tendon is used. One large incision may also be considered cosmetically less preferable than two smaller ones, and may take longer to heal. This system as disclosed is preferably used with the guide or ruler elevated above the tendon and also outer-most layers and skin of patient, spaced away (anteriorly) from the target tissue (similar to a bridge). This will provide improved visualization of the tendon anterior surface. This system is configured to extend through two smaller incisions through the outer layers and skin of the patient so as to provide some direct visualization of the tendon, with the aid of the elevated guide and also some obscured portions where there is no incision, that rely on the system to aid in controlled the harvesting trajectory, depth and length. This guide preferably includes a tendon harvester (cutting tool) that cooperates with the guide to maintain a desired cutting trajectory and thereby forming two parallel lateral surfaces of a graft in a single motion while limiting a trajectory of the tendon harvester as it moves along the QT. The system also includes features to limit any posterior migration so as to control to a more uniform graft thickness and limit any unintentional tissue injury. The guide may include a reference surface that may engage a portion of the knee anatomy such as the patella. The tendon harvester may operatively engage the guide so as to direct the pathway of the tendon harvester while cutting. In some embodiments the harvesting system may include means of selectively terminating an end of the prepared strip. The system may be used for harvesting a QT graft with or without a bone block. The specification now turns to an example system.

Figure 5:
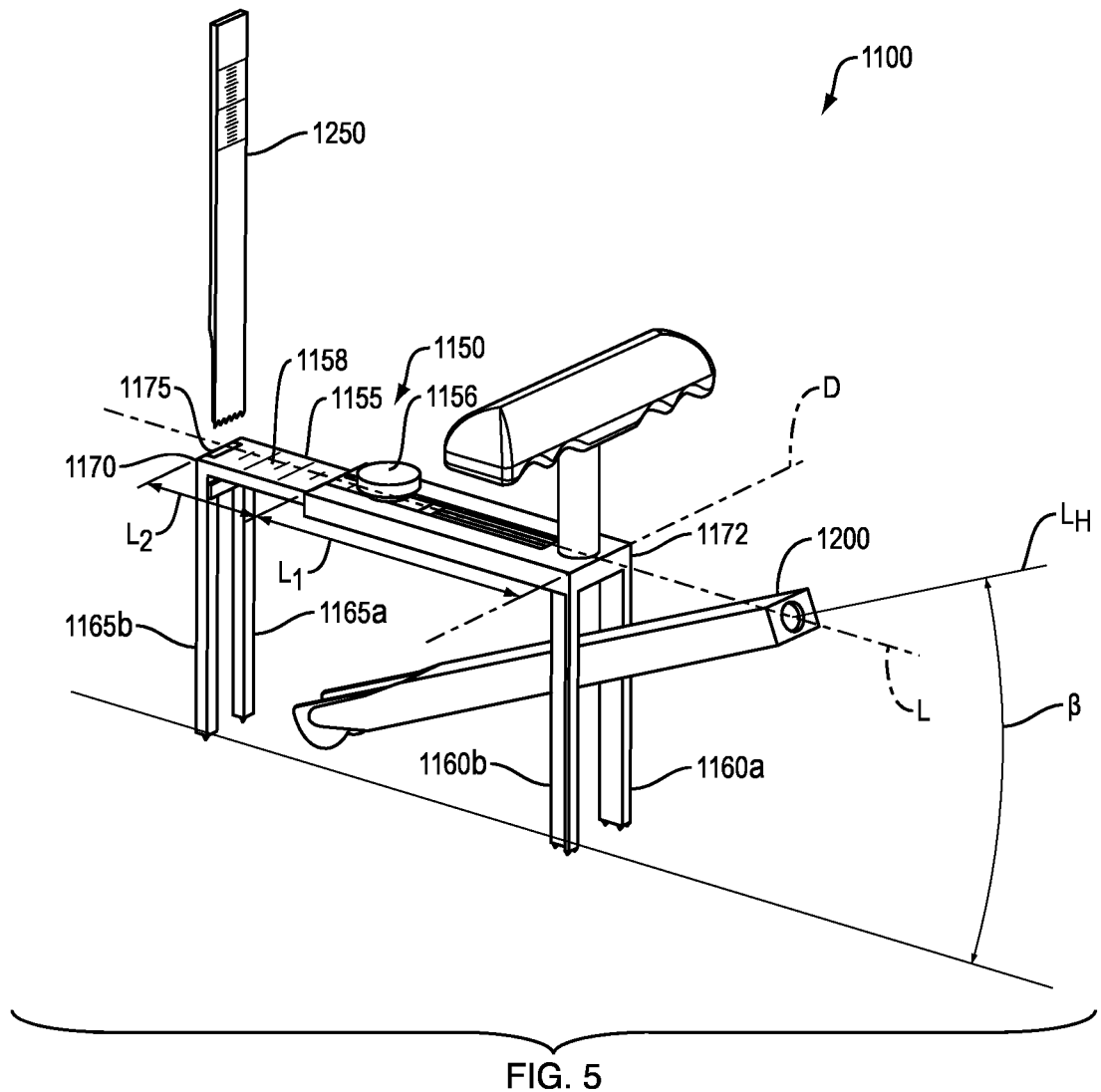
FIG. 5 schematically shows an isometric view of a harvesting system in accordance with this disclosure.

FIG. 5 presents harvesting assembly 1100 including an adjustable over-the-top guide 1150, a harvester tool 1200, and a blade 1250 for graft amputation. Guide 1150 may include bridge 1155 having an adjustable length that may be altered according the desired graft length. Adjusting length of bridge 1155 alters the distance between a first pair of legs 1160a and 1160b and a second pair of legs 1165a and 1165b. Both pairs of legs 1160a, 1160b and 1165a, 1165b may extend perpendicularly relative to longitudinal axis "L" of bridge 1155. Each pair of legs 1160a, 1160b and 1165a, 1165b may have a length sufficient to elevate the bridge 1155 above the target tendon tissue and also above and spaced away from the outer most layer of the patient. Each pair of legs 1160a, 1160b and 1165a, 1165b may be equivalent in length to each other to maintain the bridge 1155 parallel to the tendon anterior surface. The range of leg lengths may be between 5 and 10 cm to accommodate for different patient sizes with a range of outer layer thickness for ranges in patient sizes. Legs lengths may in some embodiments be adjustable. For example some patients may have outer layers greater than 2 cm such that the tendon anterior surface is at least a few centimeters below the patient skin. The bridge 1155 is preferably spaced anteriorly away from the tendon tissue and skin, in use, such that the tendon surface may be viewed and not obscured by the bridge 1155.

The first pair of legs 1160a and 1160b may preferably extend through a first incision adjacent the patella. The second pair of legs 1165a and 1165b may preferably extend through a second incision adjacent a tendon proximal end. The first and second incision may not be continuous with each other and the second incision may be perpendicular relative to the first incision. The first incision may extend parallel to the bridge 1155 and along a length of the QT, and may be sufficiently sized to laterally expand to view the patellar end of the QT and receive the first pair of legs 1160a and 1160b. The second incision may be laterally oriented across the patient thigh and about as long (laterally) as the spacing between the two legs of the second pair of legs 1165a and 1165b. The two legs of the second pair of legs 1165a and 1165b may therefore span the length of the second incision such that the first leg 1165a is disposed at a first end of the second incision and the second leg 1165b is disposed at the opposing end of the second incision. Bridge length may be adjusted and fixed in position with a tightening screw or knob 1156. Bridge may include a ruler or marks 1158 indicating a bridge length. Marks 1158 may be indicative of an overall length of desired graft and therefore may include numbers and units such as inches or centimeters. As such numerical values may be smallest in value closest to end 1170 approximately equal to length L1 and increase in numerical value as the numbers are positioned closer to end 1172.

Figure 6:
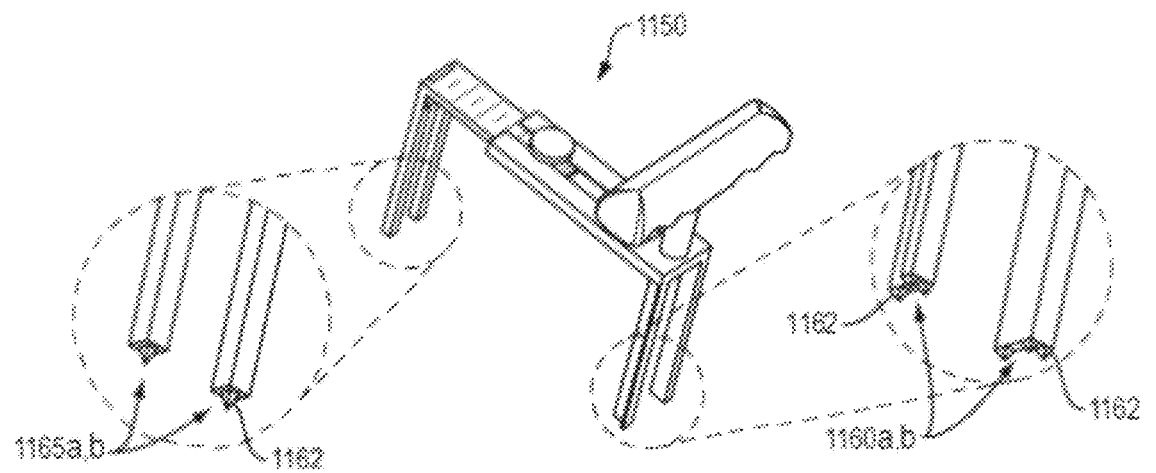
FIG. 6 schematically shows a guide of the harvesting system illustrated in FIG. 5 in accordance with this disclosure.

FIG. 6 shows guide 1150, include a first pair of legs 1160a, 1160b, and a second pair of legs 1165a and 1165b. At least some of the legs may terminate with teeth configured to engage or grip tendon tissue and therefore may include at least one barb, piercing tip or tooth 1162. This will reduce likelihood for guide 1150 to slip.

Figure 7A:
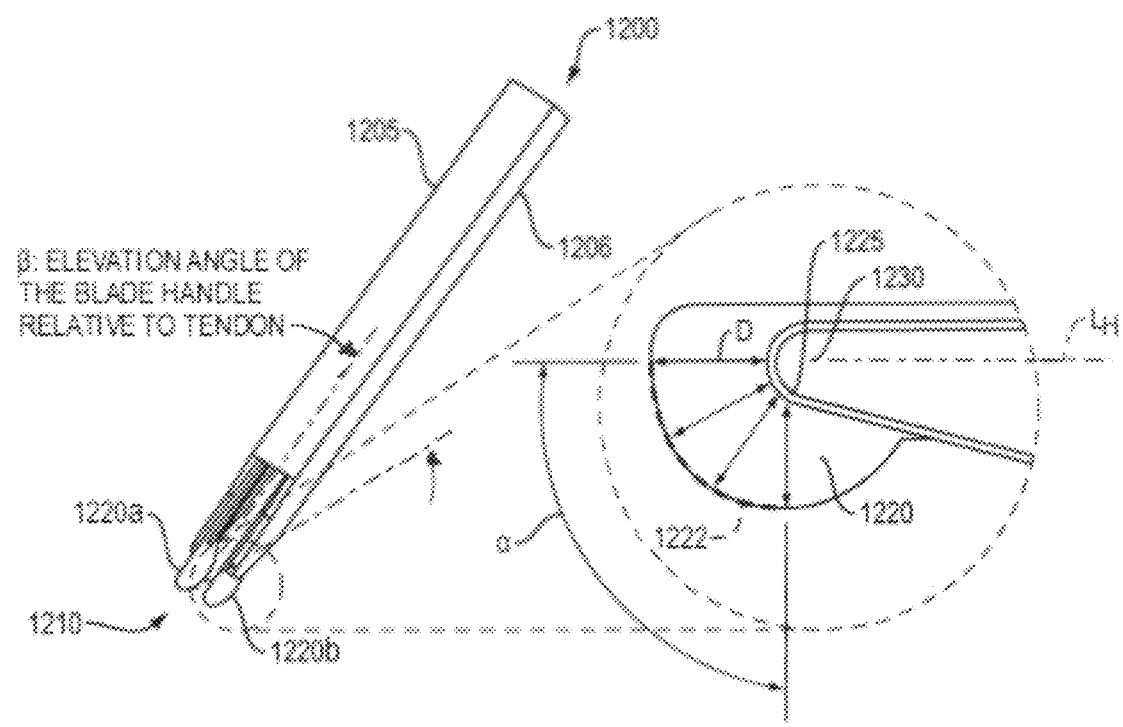
FIGS. 7A-7C schematically show a variety of views and method of use of a harvester of the harvesting system illustrated in FIG. 5 in accordance with this disclosure.
Figure 7B:
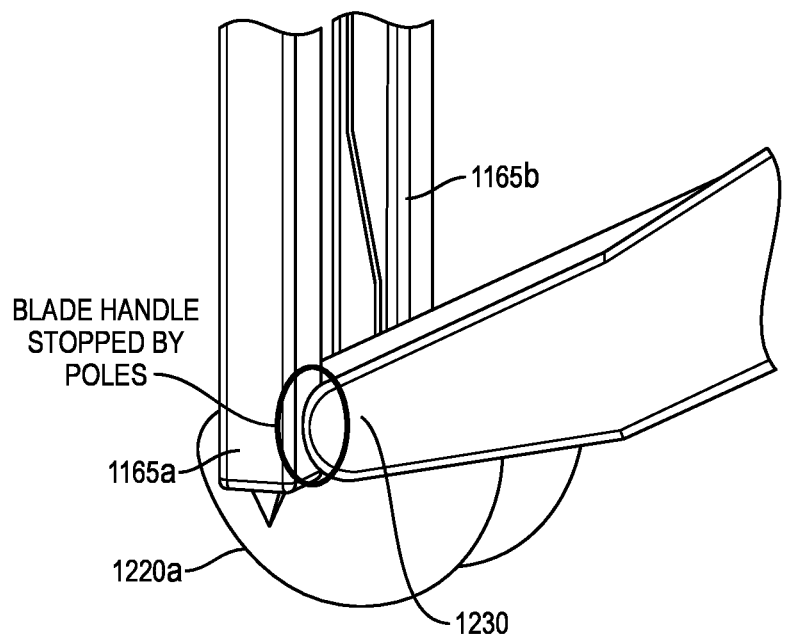
Figure 7C:
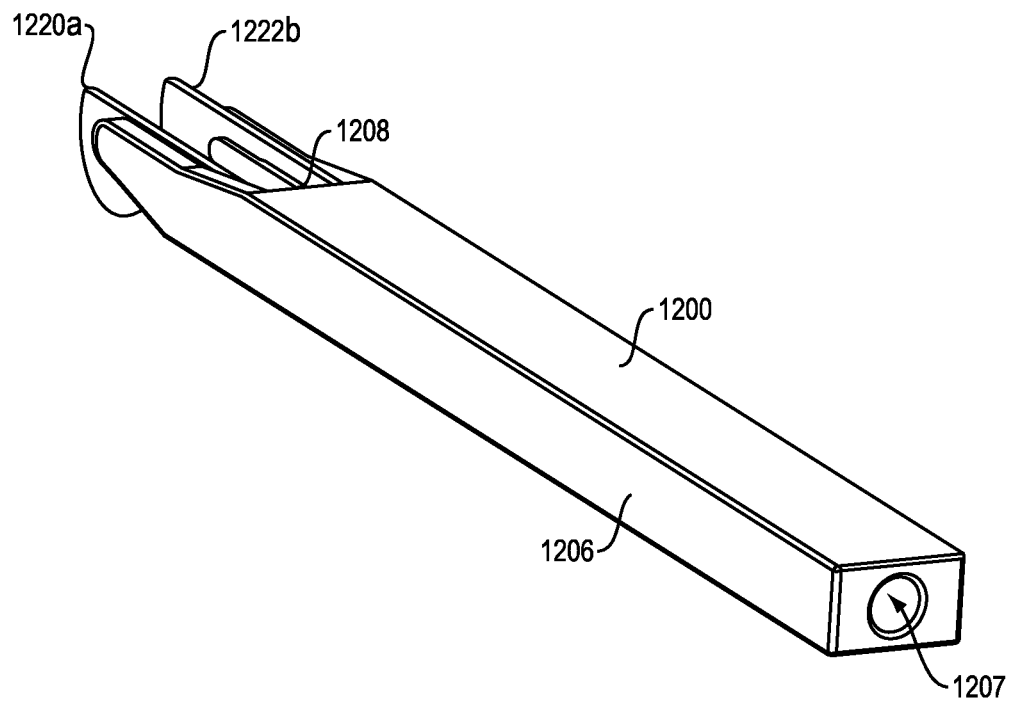
Figure 8A:
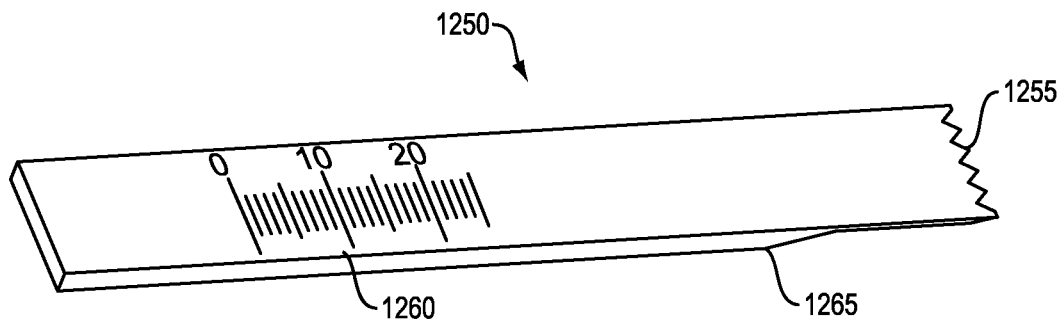
FIG. 8A schematically shows an amputating blade of the harvesting system in accordance with this disclosure.
Figure 8B:
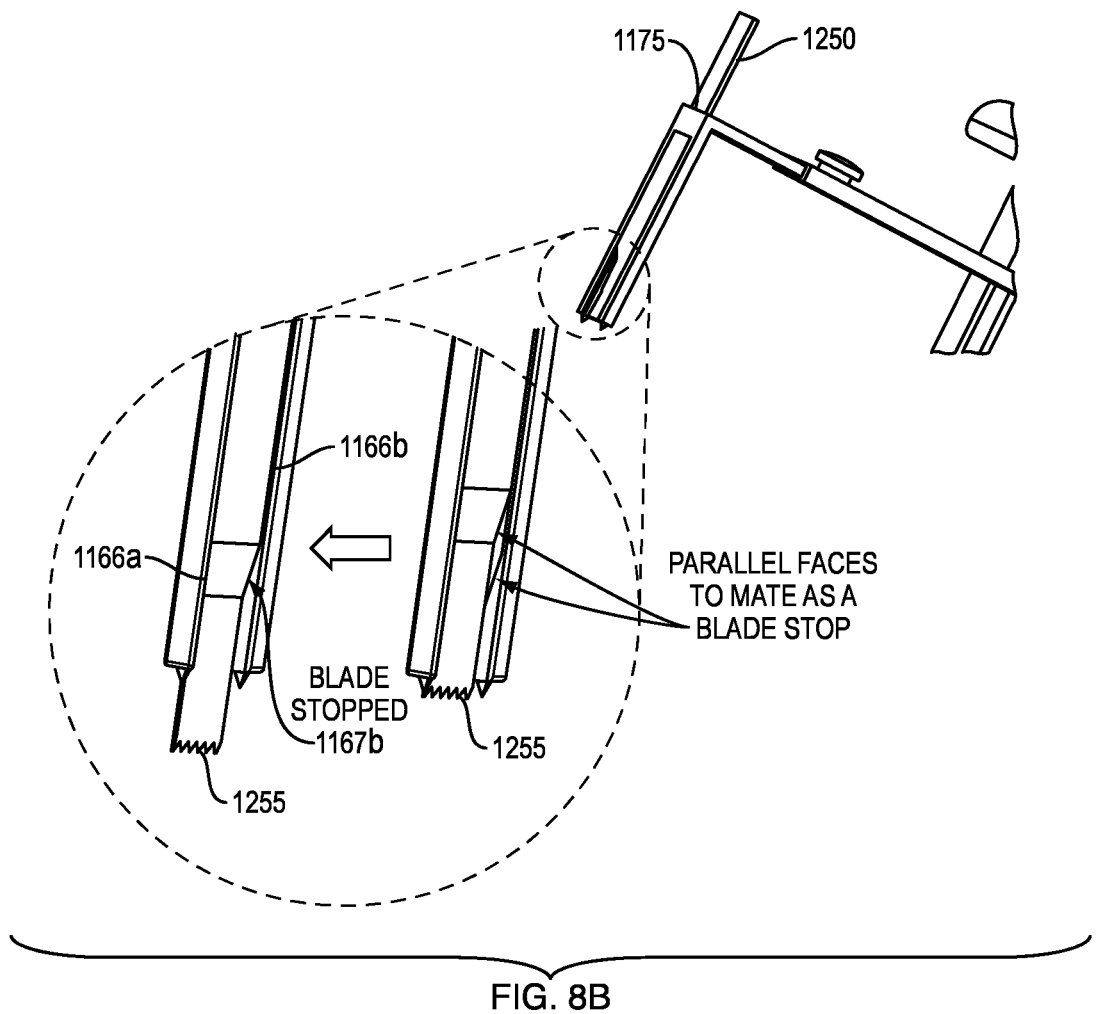
FIG. 8B schematically shows a method of amputating a tendon graft with the harvesting system in accordance with this disclosure.

Best seen in FIGS. 7A-7C, system 1100 may also include a harvester 1200 for cutting into the tendon. Harvester 1200 includes an elongate handle 1205 and two blades (1220a and 1220b) operatively coupled at a harvester leading end 1210. Each blade 1220 may be identical and parallel to each other, each blade 1220a and 1220b configured to form a lateral side of the tendon graft, simultaneously. Each blade 1220a and 1220b is configured to penetrate the tendon a limited depth D, limited by the leading edge curve of the blade 1220 in cooperation with a curved stop surface 1225. More specifically each blade 1220 defines a leading edge 1222 that extends along an arc or curve along a plane parallel to the longitudinal axis LH axis for at least angle $\alpha$, the leading edge 1222 a constant dimension equal to depth D from a closest corresponding point on a curved surface 1225 or a stop 1230. Blades may have either a combination of sharp edge (to cut tissue) and dull edge (to separate tissue); or a separate sets of sharp/dull ones. Arc length a may extend approximately 90 degrees, so as to accommodate a variety of elevation angles $\beta$ of the blade handle longitudinal axis LH relative to the tendon exterior (anterior) surface (seen in FIG. 5). The range of angles $\beta$ may be between 5-80 degrees relative to tendon surface. As the harvester 1200 extends along the tendon, and under the patient skin between the first and second incision, the elevation angle $\beta$ may generally reduce. The harvester axis LH may rotate towards a more parallel orientation relative to the tendon anterior surface. This curved leading edge 1222 and curved surface 1225 may preferably control the depth of cut into the tendon for this range of elevation angles $\beta$. Therefore this curved leading edge 1222 and curved surface 1225 may preferably enable the surgeon to create a constant depth of cut as he or she moves the harvester 1200 along the tendon and alters the elevation angle $\beta$.

Stop 1230 may also be configured to engage the second pair of legs 1165a, 1165b to define a length of cut along the tendon. As such the second pair of legs 1165a, 1165b are spaced apart so as to receive the blades 1220a, 1220b therethrough and engage a leading surface of the stop 1230 to halt any further translation of the blades 1220a and 1220b (FIG. 7B). Harvester handle 1205 is shaped to extend between and engage the first pair of legs 1160a or 1160b to limit the trajectory plane of the harvester 1200 while allowing the harvester 1200 to rotate and adjust its elevation angle $\beta$. Seen best in FIGS. 5 and 7C harvester handle 1205 may have two parallel sides 1206 that may engage and slidingly fit between the first pair of legs 1160*a* and 1160*b* and thereby control the trajectory plane along the guide 1150 and along the tendon surface. Harvester handle 1205 may therefore have a width that is approximately equal to the spacing between the first pair of legs 1160. Harvester 1200 may also including a lumen 1207 for receiving a scope or light source therethrough. Lumen may extend up to the blade end 1208 of harvester 1200 to place a scope or light source adjacent the blades 1220 to better visualize harvesting. In alternative embodiments handle 1205 may include an externally located clasp or snap for selectively engaging to a scope or light source.

System 1100 may also include a means of terminating or amputating an end of the graft, the means including a blade 1250. Blade 1250 may have a sharp and/or serrated end 1255 for slicing through tissue. A serrated end 1255 may be preferable as it may grasp tissue better and be less likely to slip while slicing. Blade 1250 may also include length indicators 1260, indicative to the depth of cut into the tissue. Blade 1250 may also include a means of limiting the depth of cut into the tissue, which may include a tapered surface 1265 that tapers the blade thickness. Alternatively the blade thickness may have an orthogonal step in thickness. Guide end 1170 may include a slot 1175 for receiving the blade 1250 and the second pair of legs 1165*a*, 1165*b* may include rails or slots 1166*a*, 1166*b* for sliding the blade 1250 therealong and thereby limiting the orientation of the blade 1250. As shown rails 1166*a*, 1166*b* may include a ramp 1167*a*, 1167*b* configured to engage tapered surface 1265 and limit how deep blade end 1255 cuts into the tendon. In an alternative embodiment at least one of the second pair of legs 1165*a*, 1165*b* may have a pin or orthogonal protrusion (not shown) extending from an internal surface of leg 1165*a* or 1165*b* to halting the blade motion. Pin may engage an orthogonal step in thickness of the blade 1250 for example. Furthermore at least one of second pair of legs 1165*a*, 1165*b* may have a series of spaced holes along and through the leg, each hole sized to receive a pin therethrough, therefore allowing the surgeon the ability to choose a pin location and thereby an amputation depth into the tendon. In some embodiments a second slot may be located at end 1172 for receiving blade 1250 and also amputating a patellar end of graft. The first pair of legs 1160*a*, 1160*b* in this embodiment may therefore also have corresponding rails and pins similar to those described for the second pair of legs 1165*a*, 1165*b*.

Figure 9:
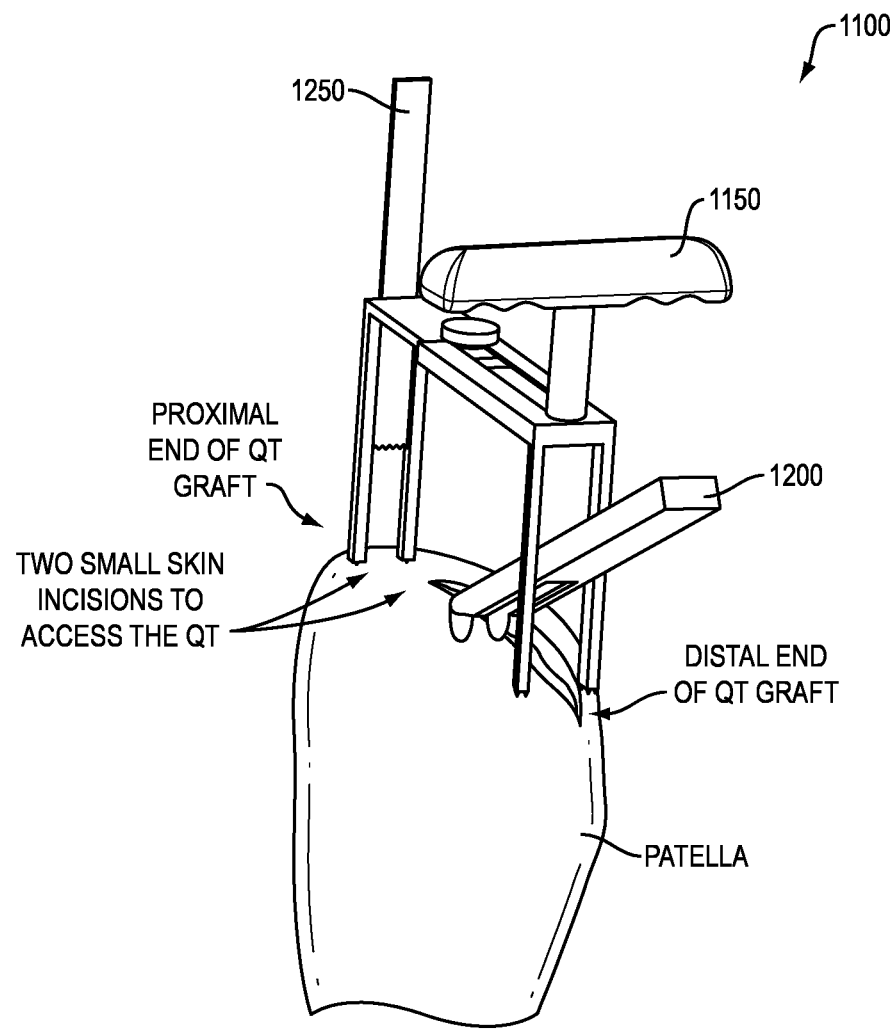
FIG. 9 schematically shows a method of use of a harvesting system illustrated in FIG. 5 in accordance with this disclosure.

Turning now to FIG. 9, a method of forming a tendon graft is represented using system 1100, the method including making a first incision adjacent a patella and through a patient's skin up to the anterior surface of the QT. The first incision may gain access to the north pole of patella. The first incision may extend along the QT a first length. A second incision may then be formed through a patient's skin up to an anterior surface of the QT, adjacent a proximal end of the QT. The second incision may be formed at least partially by a serrated blade 1250 of system 1100 (or by a scalpel). The second incision may extend laterally across the patient's thigh and may be a discrete incision spaced away from the first incision. The second incision may alternatively be two smaller incisions, one each to receive a leg (1165*a*. 1165*b*) of the system 1100. An adjustable bridge 1155 may be adjusted to a desired length of tendon graft. The first incision may be retracted to expose a portion of the QT and a first pair of legs 1160*a*, 1160*b* may be placed on the QT anterior surface adjacent the patella. A second pair of legs 1165*a* and 1165*b* may be placed through second incision to engage the anterior surface of QT. Each of the second pair of legs 1165 may be at opposing ends of second incision. At least some of the first and second pair of legs may engage and penetrate the anterior surface of QT with teeth or piercing tips disposed at free ends of the corresponding legs. These teeth may limit displacement/slippage of the guide 1150 throughout the whole process of harvesting. With the legs engaged with the QT, the legs have a length sufficient to elevate the adjustable bridge 1155 above and spaced away from the patient's skin.

The method may further include extending a harvester 1200 between the first pair of legs 1160*a*, 1160*b* and placing a curved leading edge of a harvester blade 1220 into the QT tissue. The curved leading edge 1222 may cooperate with a stop surface 1225 to limit the depth of cut into the QT. The method may then include translating the harvester 1200 along the QT and towards the second pair of legs 1165*a*, 1165*b*. The method may alternatively include translating the harvester 1200 along the QT and away from the second pair of legs 1165*a*, 1165*b*. The harvester handle may slidingly fit between the first pair of legs 1160*a*, 1160*b* so as to maintain a targeted trajectory plane during harvester translation. The method may further include translating the harvester 1200 along the QT up until the stop 1230 abuts the second pair of legs 1165*a*, 1165*b*. The method may further include beginning to translate the harvester 1200 along the QT with the harvester 1200 at a first elevation angle β relative to the tendon anterior surface, and wherein this angle may range between 0 and 80 degrees. The method may further include beginning to translate the harvester 1200 along the first incision, followed by under a patient's outer layers of tissue including the patient' skin and up to the second incision. The method may further include beginning to translate the harvester 1200 along the QT with the harvester 1200 at a first elevation angle β relative to the tendon anterior surface, and gradually reducing the elevation angle β as the harvester extends along the QT. The method may further include maintaining a constant depth of cut into the QT while translating the harvester 2100, the blade leading edge and stop surface configured to limit the depth of cut for a range of elevation angles β. The method may also include improving visualization of the cut using a light source or scope disposed adjacent the blade 220. The light source or scope may be operatively coupled to the harvester.

The method may also include amputating the tendon using a blade 1250. Blade 1250 may be translated along rails formed along the second pair of legs 1165*a*, 1165*b* and through the second incision. Blade 1250 may penetrate tendon tissue up until a stop surface or pin associated with the second pair of legs 1165*a*, 1165*b* abuts a corresponding stop or surface on blade 1250.

Tendon Amputating Devices

Figure 10A:
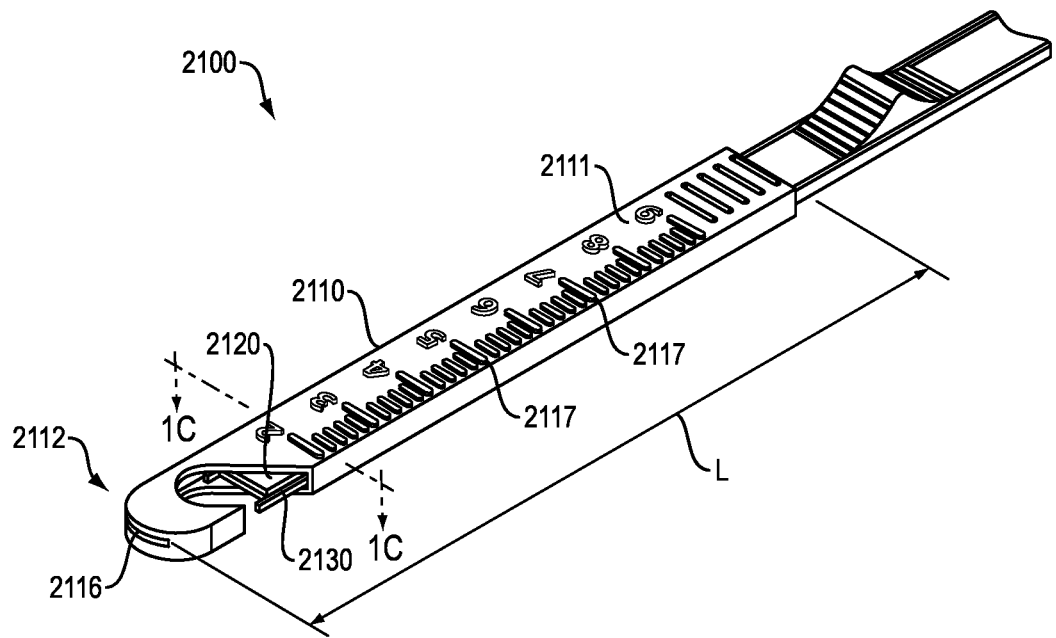
FIG. 10A schematically shows an isometric view of an amputating device in accordance with this disclosure.

FIG. 10A shows a first embodiment of a device 2100 for truncating or amputating an attached end of a prepared tendon strip. This device 2100 is preferably applicable once a length of the tendon has been formed into a strip and still has an end attached to the native tendon for example. The device 2100 may then wrap around the strip and cut across the thickness of the preformed strip resulting in a free end of the tendon graft strip. Device 2100 generally includes three components, a sleeve 2110, a clamp 2130 and a cutting tool 2120. Clamp 2130 and cutting tool 2120 are both coaxially disposed within the sleeve 2110 and axially slideable along the sleeve 2110. Clamp 2130 and cutting tool 2120 may extend out of an opening at a handle end or gripping end of sleeve 2110, so as to be pushed or pulled to axially. Sleeve 2110 defines an elongate rectangular slot 2119 for receiving clamp 2130 and cutting tool 2120. Clamp 2130 cooperates with the sleeve 2110 to selectively axially slide to engage a tendon strip, and or clamp on the tendon strip. Cutting tool 2120 cooperates with the sleeve 2110 to selectively axially slide and transect the tendon strip. Sleeve 2110 defines a hooked distal end 2112 the hook defining a lateral opening 2114 configured to thread under and partially wrap around the tendon strip cross section. Tendon strip may be attached at both ends and therefore may not readily be threaded through a completely enclosed aperture without detaching at least one end, such as the end adjacent the patella for example. Beyond the lateral opening 2114 is an opening 2115 to a hooked end cavity 2113 configured to receive and shield a leading edge of the cutting tool 2120. This cavity 2113 may be essentially an extension of slot 2119 and may have an equivalent width and thickness. A leading edge of clamp 2130 may also extend through the opening 2115 and into the hooked distal end cavity 2113. Device 2100 preferably extends along a single longitudinal axis, and is slideably operated along the same axis. Device 2100 is preferably not angled to extend off the longitudinal axis, thereby providing a simple and easy to use device. Seen best in FIG. 10C, sleeve 2110 may generally define a constant width "W" and thickness "T" along its entire length "L" except for the rounded distal end surface 2116. Sleeve outer surface may include reference markers 2117 for the surgeon to estimate the length of tendon strip before amputating. These reference markers may be at any locations that aid is providing length information, and may be marked in inches, centimeters or just marked at regular intervals of unspecified unit.

Figure 10B:
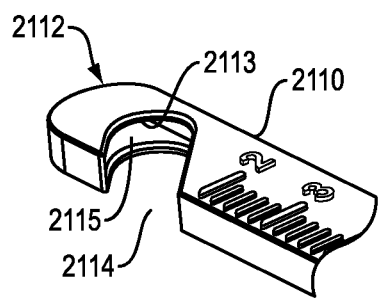
FIG. 10B schematically shows a distal end of amputating device illustrated in FIG. 10A, in accordance with this disclosure.
Figure 10C:
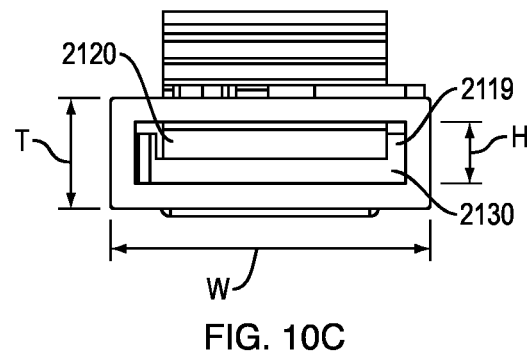
FIG. 10C schematically shows a cross section of an amputating device in accordance with this disclosure.

Best seen in FIG. 10C, clamp 2130 may have a width that slidingly engages sidewalls of the slot 2119. The inventors envision that the slot 2119 and clamp 2130 may include internally located ratchets or detents to maintain the location of clamp 2130 within the sleeve 2110 and reduce inadvertent axial movement of clamp 2130 along the slot 2119. An example ratchet is shown in later embodiments. Clamp 2130 may define a rail cross section for receiving the cutting tool 2120 therein. As such cutting tool 2120 may have a narrower corresponding width than both the clamp 2130 and slot 2119. The combined thickness of both the cutting tool 2120 and clamp 2130 may be approximately equal to the slot height (H).

Figure 10D:
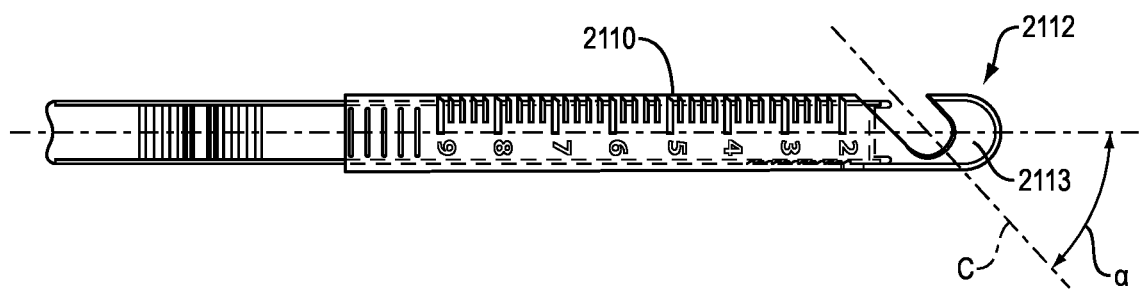
FIGS. 10D, 10E and 10F schematically show top views of an amputating device illustrated in FIG. 10A, in progressive stages of deployment in accordance with this disclosure.
Figure 10E:
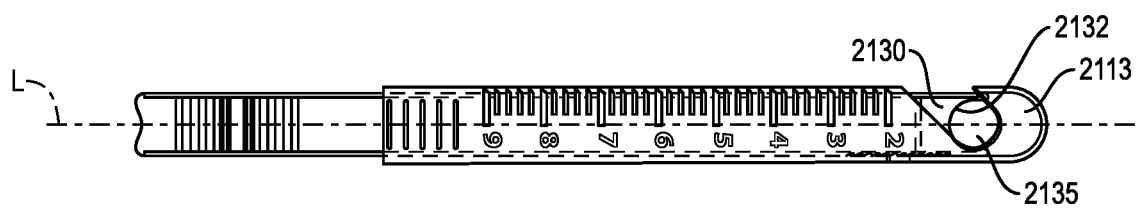
Figure 10F:
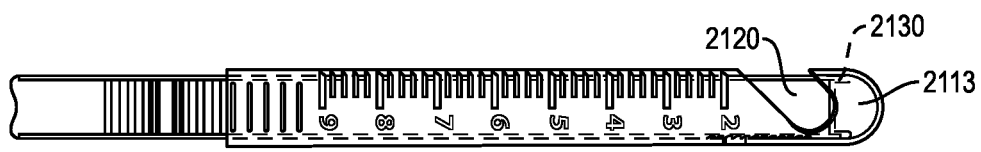

FIGS. 10D, 10E and 10F show a top view of three progressive configurations of the device 2100. In FIG. 10D, device 2100 is shown in a retracted configuration such that both the cutting tool and clamp are retracted from opening 2114 within the sleeve slot 2119. The leading edge of the cutting tool is shielded. Tendon strip cross section may be inserted into lateral opening 2114 in this configuration. FIG. 10E shows a second or enclosed configuration wherein the clamp 2130 has moved across a portion of the lateral opening 2114 so as to encircle the tendon strip disposed therein, and retain the tendons strip within the hooked distal end. FIG. 10F shows the embodiment in a clamped and transected configuration. In this configuration the clamp 2130 may have been advanced further into the cavity 2113 so as to better clamp on the tendon strip cross section and thereafter the cutting tool 2120 is advanced across the opening 2114, placing the cutting tool leading edge into the cavity 2113.

Lateral opening 2114 may have a central axis C (Seen best in FIG. 10D) that extends at an angle α relative to a longitudinal axis L-L of the device, generally oriented to ease insertion of tendon strip into opening 2114. Angle α may range from about 10 and 80 degrees, and more preferably between 30 and 60 degrees. As shown, angle α is approximately 45 degrees. Lateral opening 2114 and sleeve width "W" are generally sized to receive a tendon strip cross section. Lateral opening 2114 extend along angle α and has a substantially constant opening width, such that surfaces extend parallel to central axis C for most of the opening extent. For example sleeve width may be between 15-25 mm wide. Clamp 2130 including the leading edge of clamp 2130 may axially side along a plane that is parallel to the longitudinal axis of the device 2100. Clamp 2130 may encircle the tendon strip in cooperation with the lateral opening 2114 and retain the tendon strip within the hooked end. The clamp leading edge 2132 may be preferably shaped to cooperate with the lateral opening 2114 to fully encircle the tendon strip and form aperture 2135. Aperture 2135 may be sized to allow the tendon strip to slide therethrough so as to slide the aperture 2135 and device leading end towards the proximal end of tendon strip before amputation.

Clamp 2130 may have two positions, a first position that loosely encircles the tendon strip as shown in FIG. 10E so as to allow the tendon strip to slide therethrough, and a second more axially advanced position wherein the clamp 2130 may clamp on the tendon strip and limit the tendon from slipping and aid amputation. This second position can be seen in FIG. 10F. In this second clamping position the rails of clamp 2130 may extend up to a limit within the cavity 2113 that provides a stop, limiting further axial motion of the clamp 2130.

Cutting tool 2120 includes a sharp leading edge 2122 for transecting tough tendon tissue and may be independently operated relative to the clamp 2130. When the device distal end 2112 is in the targeted location, the cutting tool 2120 may axially slide across the lateral opening 2114 and thereby transect the tendons strip. The cutting tool 2120 may extend across the entire opening 2114 so that the sharp edge 2122 is now encircled or covered by the sleeve cavity 2113. The tendon strip may now be free at this end (and may still be attached at the opposite end, at the patella). Having the sharp edge 2122 covered in this cut configuration first of all helps ensure that the tendon is completely transected and also protects the device 2100 from unintentionally cutting non-target tissue while withdrawing the device from the incision site. Sharp leading edge may be a blade and extends and moves along a single plane parallel to the longitudinal axis of the device 2100. Sharp leading edge extends and moves along a single plane parallel to the sleeve top surface 2111.

Figure 11A:
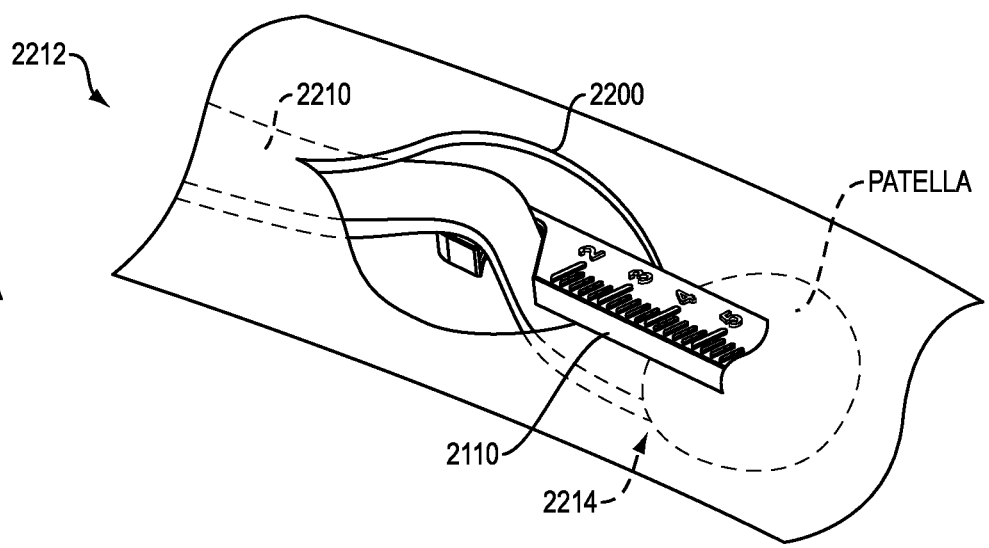
FIGS. 11A-11C schematically represent a method of amputating a tendon strip in accordance with this disclosure.
Figure 11B:
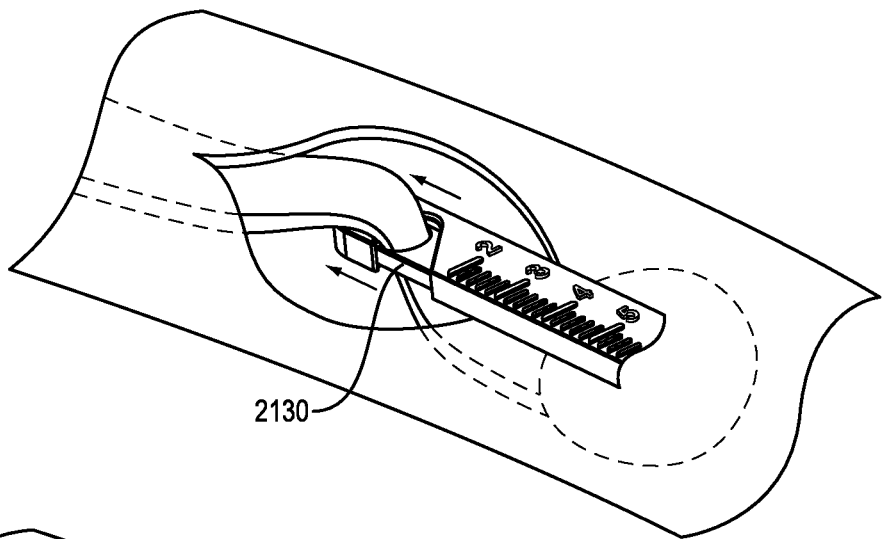
Figure 11C:
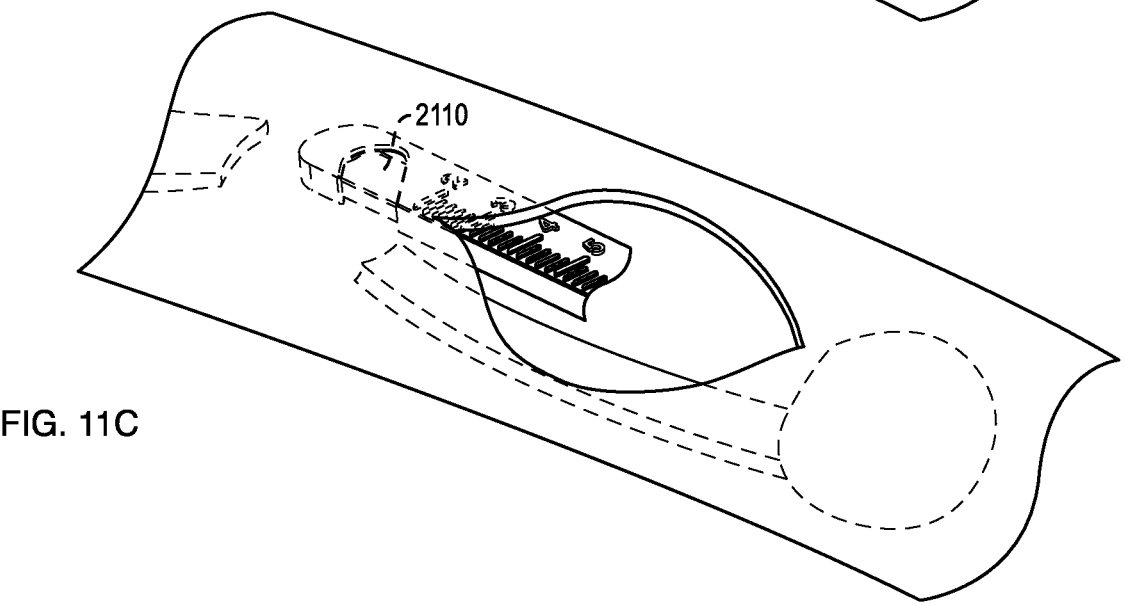

A method is represented in FIGS. 11A-11C of amputating a tendon strip and may include making a small incision 2200 adjacent the patella end of the QT and forming an elongate strip 2210 of dissected QT, the strip dissected on a medial, lateral and posterior side; the elongate strip coupled at both ends including a proximal most end 2212 adjacent the quadriceps muscle and the opposing end 2214 proximal the patella. Adjacent the small incision 2200, the tendon strip cross section may be placed through the lateral opening 2114 as shown in FIGS. 10B and 10D. A clamp 2130 of the device may be axially slid along the lateral opening to encircle the tendon strip cross section, seen best in FIGS. 10E and 11B. The amputation device 2100 may be advanced along the tendon strip under the skin and towards the attached proximal end 2212 of the strip. The clamp 2130 may then be advanced further to more tightly clamp on the tendons strip cross section and a cutting tool 2120 of the amputation device 2100 may be axially slid across the lateral opening 2114 and into a distal cavity 2113 of the device to as to transect the tendon strip cross section and be covered by the device distal portion, represented in FIG. 11C.

Figure 12A:
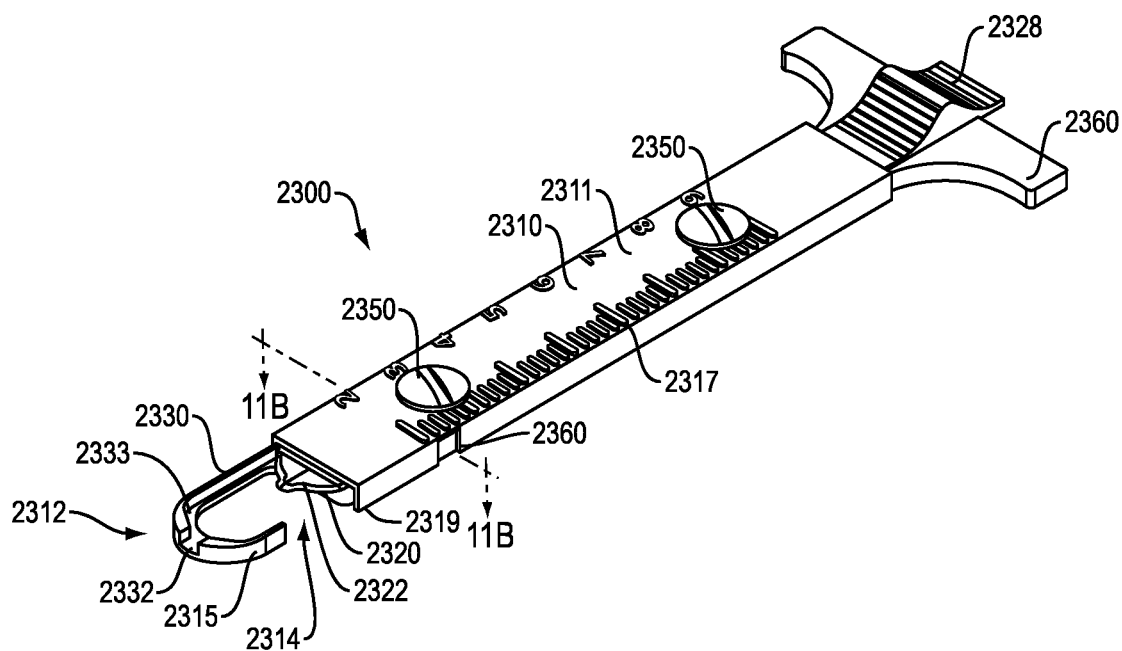
FIG. 12A schematically shows an isometric view of an amputating device in accordance with this disclosure.
Figure 12B:
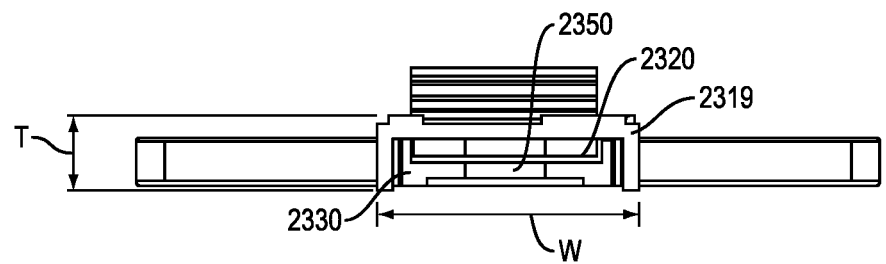
FIG. 12B schematically shows a cross section of amputating device illustrated in FIG. 12A in accordance with this disclosure.

FIG. 12A schematically shows a second embodiment of a tendon strip amputation device 2300, heretofoth named "device" 2300. Device 2300 generally includes three components, a housing 2310, a hook 2330 and a cutting tool 2320. Hook 2330 and cutting tool 2320 are both coaxially disposed within the housing 2310 and axially slideable along the housing 2310. More specifically the housing 2310 defines an elongate channel 2319 for slidingly receiving hook 2330 and cutting tool 2320. Hook 2330 and cutting tool 2320 cooperate with the housing 2310 to selectively axially slide to engage a tendon strip, clamp on the tendon strip and/or transect the tendon strip. Hook 2330 defines a lateral opening 2314 configured to thread under and partially wrap around the tendon strip cross section. Tendon strip is typically attached at both ends and therefore is not readily threaded through a completely enclosed aperture without detaching at least one end, such as the end adjacent the patella for example. Hook has a free leg 2315 that extends from a distal most end of device back towards the housing 2310 so as to help maintain tendon strip within opening 2314. Hook has a shelf 2333 extending around an inner curved surface of the hook 2330 and a notch 2332. Both shelf 2333 and notch 2332 are configured to receive a leading cutting edge of cutting tool 2320 and encircle and shield the cutting edge 2322. Device 2300 preferably extends along a single longitudinal axis, and is slideably operated along the same axis. Device 2300 is preferably not angled relative to the longitudinal axis, thereby providing a simple and easy to use device. Seen best in FIG. 12B, housing 2310 may generally define a constant width "W" and thickness "T" along its entire length. Housing outer surface may include reference markers 2317 for the surgeon to estimate the length of tendon strip before amputating. These reference markers may be at any locations that aid is providing length information, and may be marked in inches, centimeters or just marked at regular intervals of unspecified unit. Cutting tool 2320 and hook 2330 may be slideably coupled to housing 2310 via rivets or pins 2350 that extend though elongate slots 2365 in both the hook 2330 and cutting tool 2320 (best seen in FIG. 12C). Device 2300 may include a handle end 2360 and a raised, angled and/or textured surface 2328 configured to aid in pushing the cutting tool 2320 through the tendon tissue Best seen in FIG. 12B, hook 2320 may have a width that slidingly engages sidewalls of the housing 2310. The inventors envision that the housing 2310 and hook 2330 may include internal ratchets 2360 or detents to maintain the location of hook 2330 within the housing 2310 and reduce inadvertent axial movement of hook 2330 along the housing 2310. An example ratchet is shown in later figures. Hook 2330 may define a rail cross section for receiving the cutting tool 2320 therein. As such cutting tool 2320 may have a narrower corresponding width than both the clamp 2130 and slot 2119. The thickness of both the cutting tool 2120 and clamp 2130 may be approximately equal to the slot height (H)

Figure 12C:
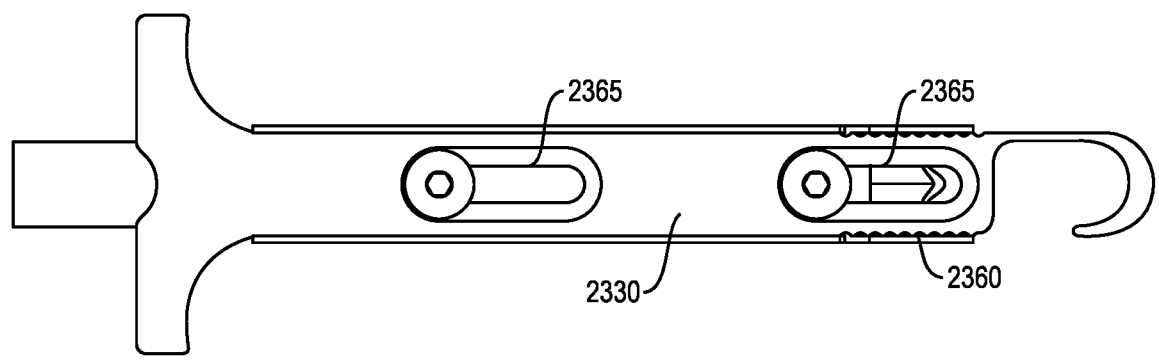
FIG. 12C schematically shows an under-side of amputating device illustrated in FIG. 12A in accordance with this disclosure.
Figure 12D:
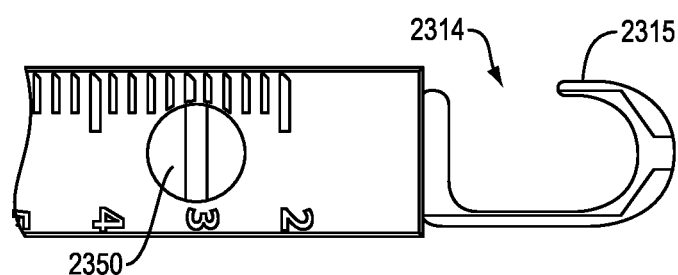
FIG. 12D schematically shows a distal end of the embodiment shown in FIG. 12A in accordance with this disclosure.
Figure 12E:
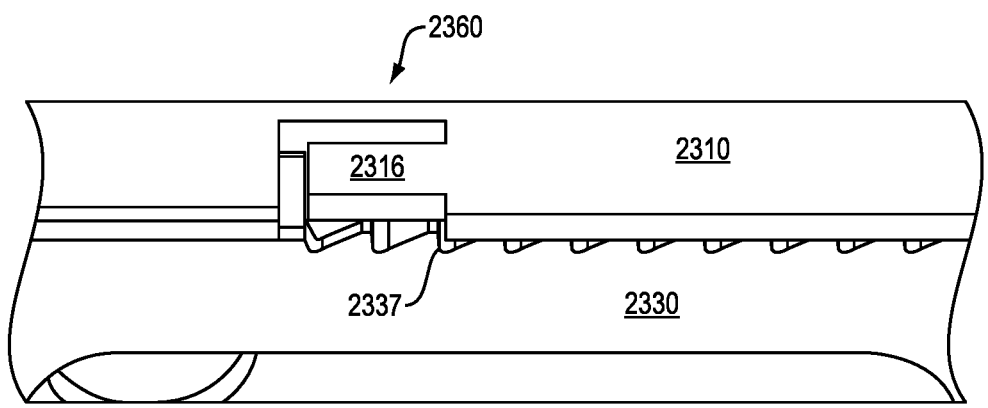
FIG. 12E schematically shows an example ratcheted portion of amputating device shown in FIG. 12A, in accordance with this disclosure.

FIG. 12C shows an underside of embodiment facing the hook 2330 with at least 2 elongate slots 2365 for receiving pins 2350 and slideable coupling the hook 2330 to the housing 2310. Ratchet portion 2360 is also shown. FIG. 12D shows a close up of hook 2330 having a free end 2315 and a lateral opening 2314. FIG. 12E shows ratchet 2360 wherein the housing 2310 may include a resilient leg 2316 shaped to selectively engage with teeth 2337 along outer lateral surface of hook 2330.

Figure 13A:
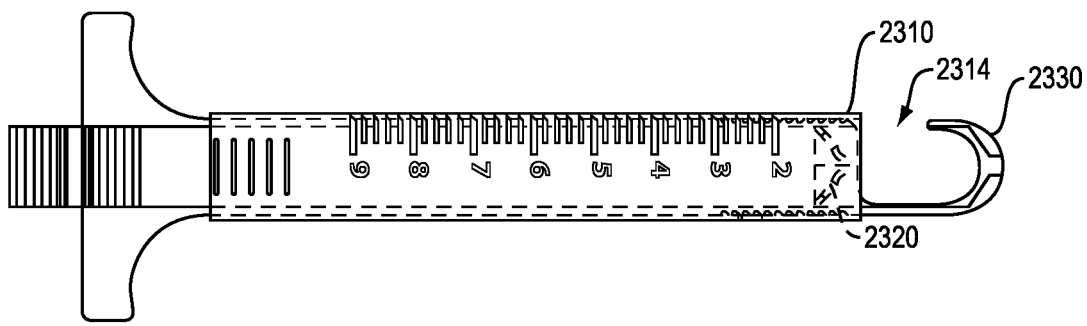
FIGS. 13A, 13B and 13C schematically show top views of the embodiment shown in FIG. 12A in progressive stages of deployment in accordance with this disclosure.
Figure 13B:
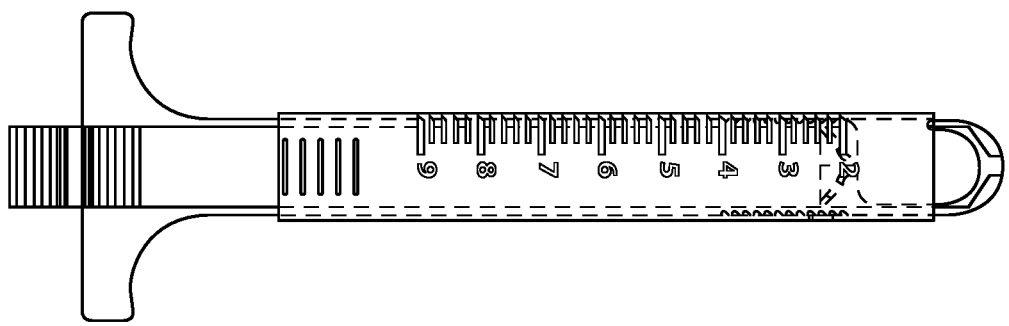
Figure 13C:
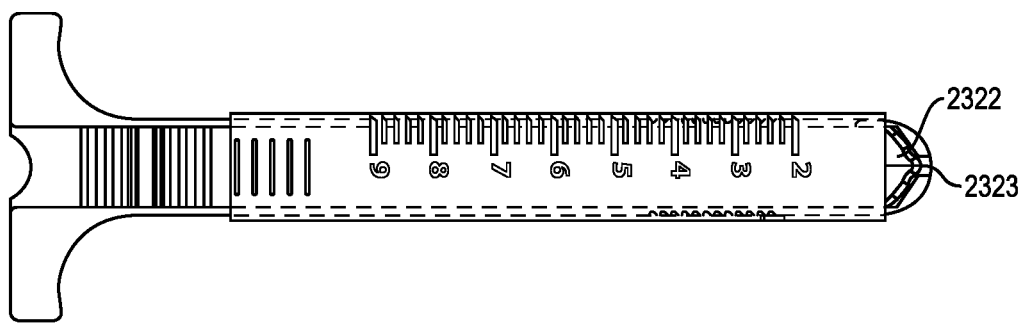

FIGS. 13A, 13B and 13C show a top view of three progressive configurations of the device 2300. In FIG. 13A, device 2300 is shown in a retracted configuration such that the hook 2330 is spaced away from the housing 2310 defining lateral opening 2314 for receiving a tendon strip cross section. FIG. 13B shows a second or enclosed configuration wherein the hook 2330 has moved such that free end 2315 engages and may enter a distal end of housing 2310 so as to encircle a tendon strip disposed therein, and retain the tendons strip between the housing 2310 and hook 2330. FIG. 13C shows the device 2300 in a clamped and transected configuration. In this configuration the hook free end 2315 may have moved further into housing 2310 and a leading cutting edge 2322 have been advanced across the hook 2330 so as to engage a distal surface of the hook 2330 and place a notched end 2323 of cutting tool 2320 into a corresponding notch of the hook 2330. Leading cutting edge 2322 may define a serrated arrow blade.

Hook 2330 may axially side along a plane that is parallel to the longitudinal axis of the device 2300. Hook 2330 may encircle the tendon strip in cooperation with housing 2310 and retain the tendon strip within the hook 2330. Hook 2330 may have two positions, a first positon that loosely encircles the tendon strip as shown in FIG. 13B so as to allow the tendon strip to slide therethrough, and a second position wherein the hook 2330 may clamp on the tendon strip and limit the tendon from slipping and aid amputation. This second position can be seen in FIG. 13C. Ratchet teeth 2337 and resilient member 2316 may be positioned to have a first tooth for the first position and a second tooth of the ratchet teeth 2337 for the second position. Cutting tool 2320 includes a sharp leading edge 2320 for transecting tough tendon tissue and may be independently operated relative to the hook 2330. When the device end 2312 is in the targeted location, the cutting tool 2320 may axially slide across the opening 2314 and thereby transect the tendon strip. The cutting tool 2320 may extend across the entire opening 2314 so that the sharp edge 2322 is now encircled, partially covered to be circumferentially shielded by the hook 2330. The tendon strip may now be free at this end (and may still be attached at the opposite end, at the patella). Having the sharp edge 2322 shielded in this cut configuration first of all helps ensure that the tendon is completely transected and also limits the device 2300 from unintentionally cutting non-target tissue while withdrawing the device from the incision site. Sharp leading edge 2322 may extend along a single plane parallel to the longitudinal axis of the device 2300. Sharp leading edge 2322 slides along a single plane parallel to the housing top surface 2311.

Figure 14A:
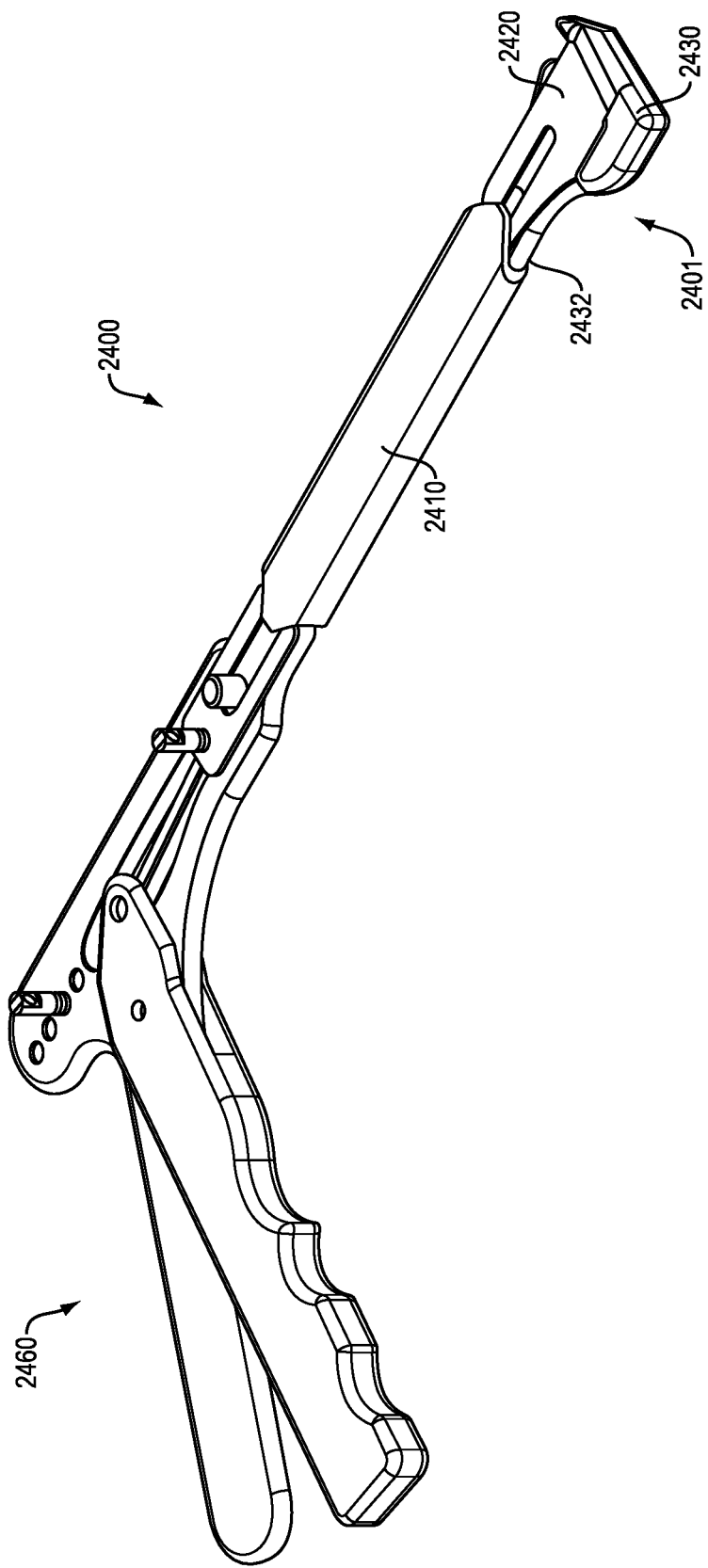
FIGS. 14A-14E schematically show an embodiment of a device for amputating a strip of tissue in accordance with this disclosure.
Figure 14B:
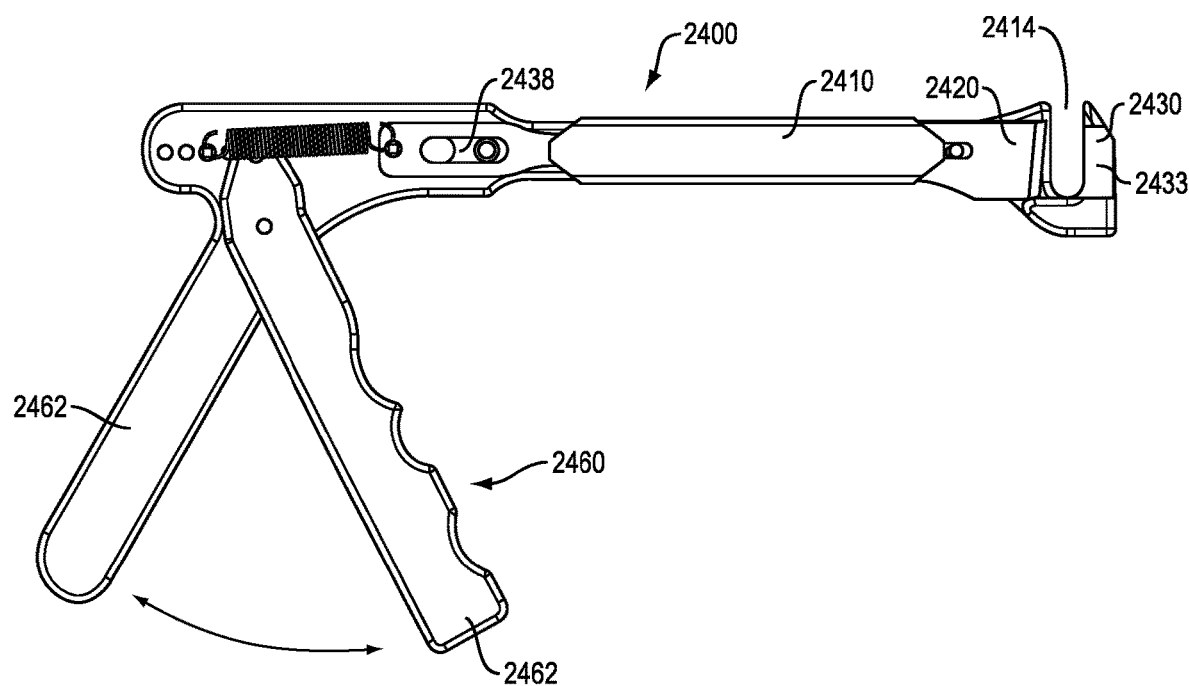
Figure 14C:
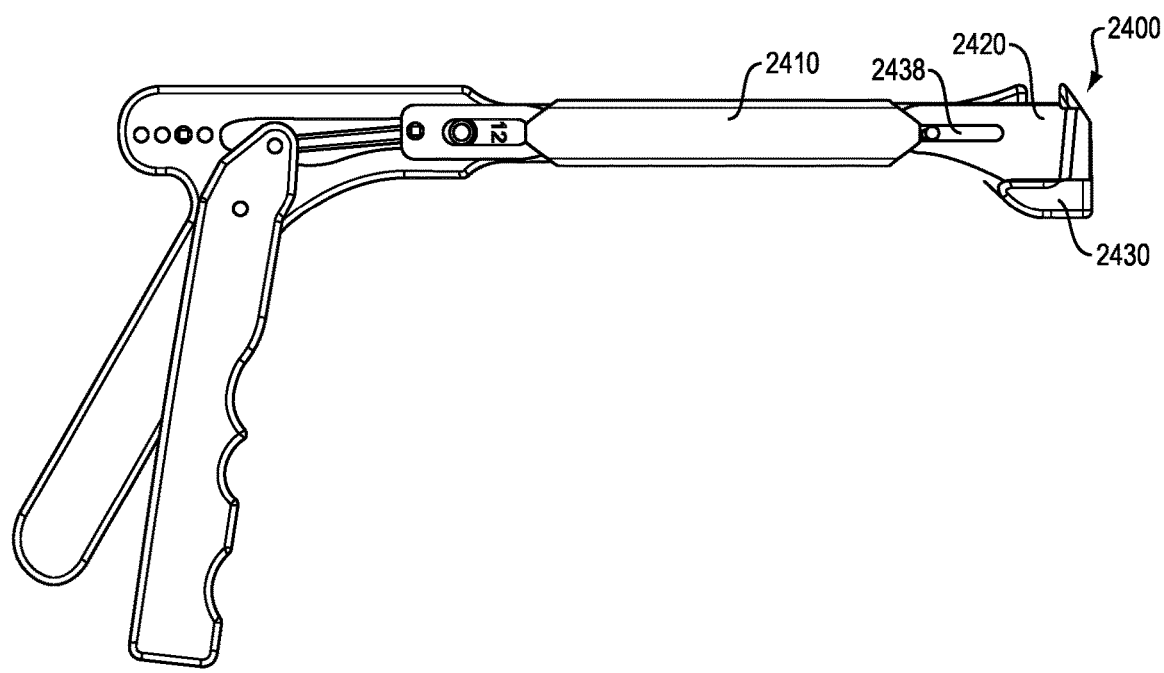
Figure 14E:
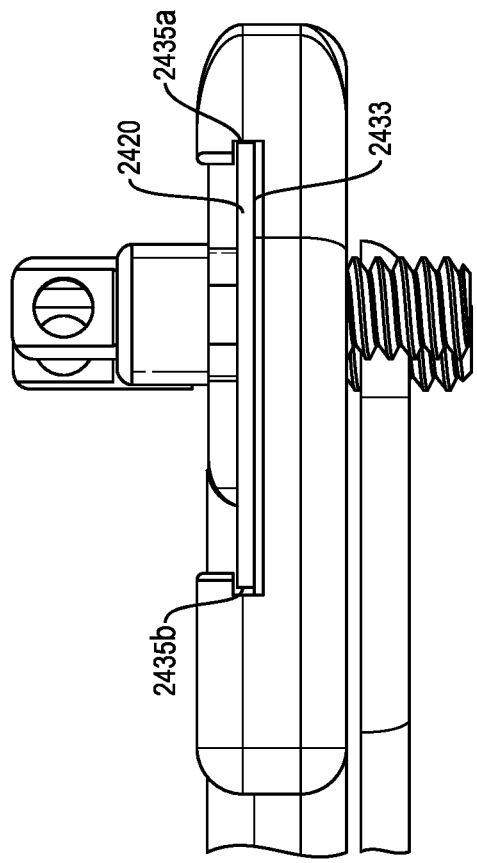
Figure 14D:
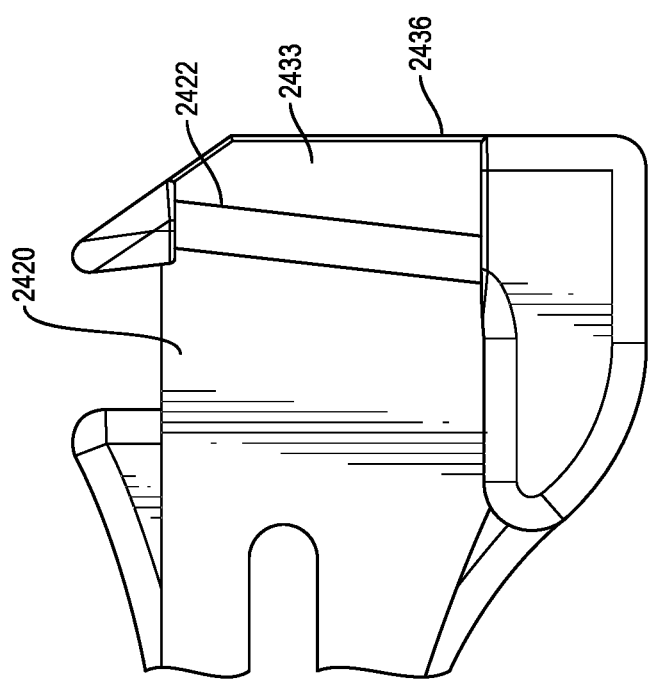

FIG. 14A illustrates a third embodiment of a device 2400 configured to transect a prepared strip of tendon tissue. Device 2400 defines a working end 2401 and a handle end 2460. Working end 2401 includes a shaft 2432 terminating with a hook 2430 and a blade 2420. Shaft 2432 and blade 2420 are both disposed axially adjacent each other and within housing 2410; blade 2420 is slideable along the housing 2410. The housing 2410 may defines an elongate channel for slidingly receiving blade 2420, for keeping the blade trajectory aligned along the longitudinal axis as the blade 2420 slides back and forth. Hook 2430 is sized to axially slide along a tendon strip with blade 2420 retracted (FIG. 14B), and then hook 2430 and blade 2420 cooperate to transect the tendon strip; a transected position shown in FIG. 14C. Hook 2430 defines a lateral opening 2414 configured to thread under and partially encircle the tendon strip cross section. Tendon strip may be attached at both ends and therefore is not readily threaded through a completely enclosed aperture without detaching at least one end, such as the end adjacent the patella for example. Hook 2430 includes a channel 2433 (best seen in FIGS. 14D and 14E) extending along the longitudinal axis of device, having a maximum width configured to slidingly receive blade therein. Channel maximum width includes two additional channels 2435a and 2435b laterally disposed on both sides of channel 2433. These additional channels 2435a and 2435b partially enclose around lateral edges of blade 2420. These lateral channels 2435a and 2435b cover a portion of the sharp edge of blade 2420 to shield adjacent tissues from inadvertent damage. Blade 2420 is also configured to advance into channel, placing the leading cutting edge surface 2422 along the channel 2433 and proximally spaced from hook distal-most edge 2436. This also shields adjacent tissues from inadvertent tissue cutting. Hook 2430 thereby includes a means to shield the blade leading edge 2422 from adjacent tissues. Blade 2420 preferably extends along a single longitudinal axis, and is slideably operated along the same axis. Device 2400 is preferably not angled relative to the longitudinal axis, thereby providing a simple and easy to use device. Blade 2420 may be slideably coupled to housing 2410 and shaft 2432. Housing 2410 may define a snap fit plastic housing that snaps around shaft 2432 and prevents blade 2420 from buckling.

Handle end 2460 including a means to advance and retract blade 2420 operable by a user. Blade 2420 is operatively coupled to a pivoting pistol grip style handle including actuator 2462 and stationary handle 2464. Rotation or squeezing actuator 2462 towards the stationary handle 2462 advances blade 2420. In some embodiments a biasing member (shown in FIG. 14B) may be operatively coupled to the actuator 2462 such that release of the actuator 2462 automatically withdraws the blade 2420 to the position shown in FIG. 14B.

A method of amputating a tendon strip with device 2400 may therefore include making a small incision adjacent the patella end of the QT and forming an elongate strip of QT, the strip dissected on a medial, lateral and posterior side. The elongate strip may be coupled at both ends including a proximal most end adjacent the quadriceps muscle and the opposing end proximal the patella. Adjacent the small incision, the tendon strip cross section may be placed through the lateral opening 2414 of device 2400. Device 2400 may be advanced along the tendon strip under the skin and towards the attached end of the strip. A blade 2420 may be axially slid across the opening 2414 and into at least one lateral channel to transect the tendon strip cross section. In the advanced position, the blade leading edge 2422 is at least partially shielded by the device working end distal to opening 2414.

Figure 15A:
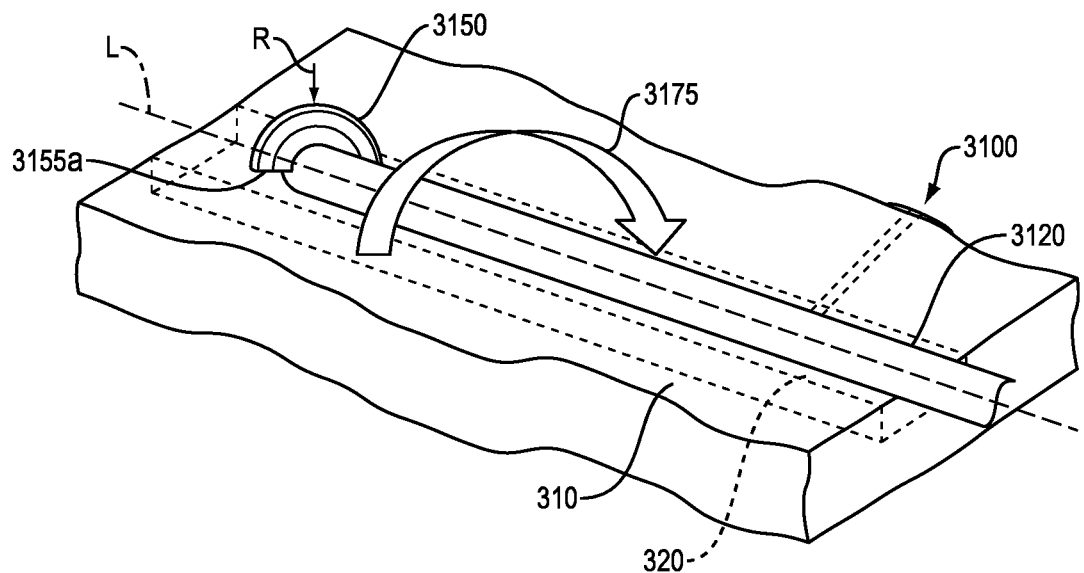
FIGS. 15A-15B schematically show an embodiment of a device for forming a transverse cut through tissue, in accordance with this disclosure.
Figure 15B:
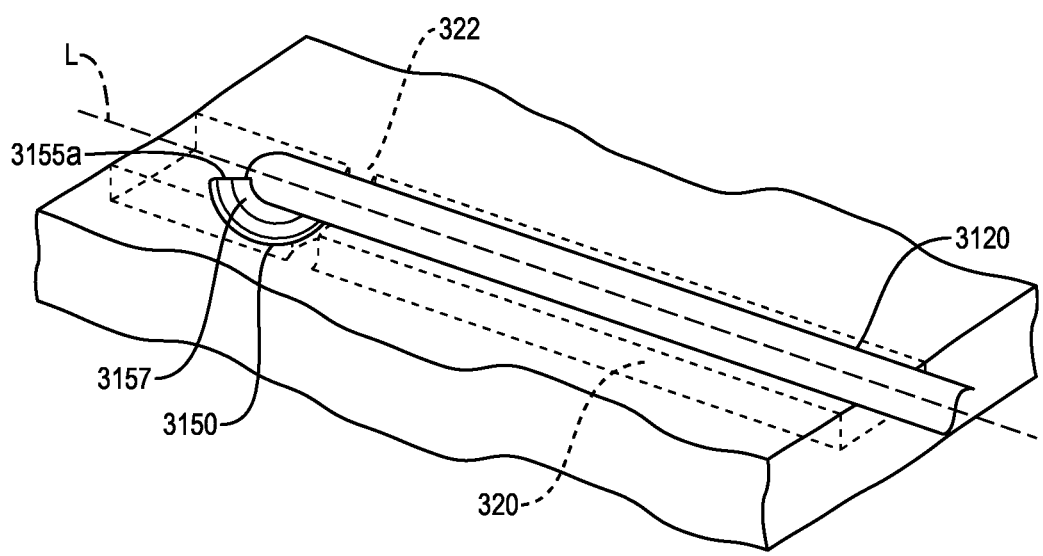

An alternative amputation device 3100 is shown in FIGS. 15A and 15B. Device 3100 includes a shaft 3120 defining a longitudinal axis L with a curved blade 3150. Blade 3150 has a radial dimension (R) that limits a depth of cut into QT 310. Blade 3150 may define a semi-circle or a segment of a circle, or may have tapered ends 3155a to ease piercing the QT tissue. Blade curved edge may extend along a plane that is perpendicular to shaft longitudinal axis.

A method of use may include preparing a graft strip 320 by performing two lateral cuts and a posterior cut. The shaft 3120 may then be slide along an anterior surface of graft strip 320 with the blade 3150 facing away from the graft strip. (FIG. 15A). Once the blade 3150 is at the desired region of the strip 320 to be truncated, defining a strip length, the shaft 3120 is then rotated around the longitudinal axis L-L to pierce the anterior surface of the QT. The shaft 3150 may continue to rotate to truncate the strip 320 (FIG. 15B). Shaft 3120 remains engaged with the anterior surface while rotating, so to control a depth of cut 232 into the QT 310 limited by blade radial dimension R. Shaft 3120 may be rotated in a first direction approximately 360 degree and resurface above the anterior surface of the QT before being withdrawn. Alternatively, shaft 3120 may be rotated approximately 180 degrees to transect the strip 320 and then a blade radial surface 3157 may withdraw the strip 320 away from the remaining QT. This device 3100 may be used with the patella end of graft strip still attached to tissue. Shaft 3120 may be rotated to partially pierce the QT and then may rotationally advance and retract in back and forth motions to gradually transect the QT.

One skilled in the art will realize the disclosure may be embodied in other specific forms without departing from the spirit or essential characteristics thereof. The foregoing examples are therefore to be considered in all respects illustrative rather than limiting of the disclosure described herein. Scope of the disclosure is thus indicated by the appended claims, rather than by the foregoing description, and all changes that come within the meaning and range of equivalency of the claims are therefore intended to be embraced therein.

The invention claimed is:

1. A tendon harvesting system for forming a target length of a graft from a native tendon comprising:
 a guide having a first end, a second end and an elongate body therebetween; the elongate body configured to be placed along the native tendon and anteriorly spaced therefrom;
 the first end being configured to engage the native tendon adjacent a patella of the native tendon;
 the second end being configured to engage the native tendon at a proximal end of the target length;
 a harvester including a first blade and a second blade, both of which are disposed at a leading end of the harvester with a handle extending therefrom; wherein the first blade and the second blade are configured to extend through the guide first end, and cut into and along an anterior surface of the native tendon disposed posterior to the first end, to form two lateral sides of the graft, the harvester being guided by the guide; and
 an amputating tool configured to transect the native tendon at the guide second end, to form a proximal end surface of the graft.

2. The tendon harvesting system of claim 1 wherein the first blade and the second blade each define curved leading edges that are parallel to each other and separated laterally from each other to form the two lateral sides of the tendon graft simultaneously.

3. The tendon harvesting system of claim 2 wherein both of the curved leading edges are equidistant from a depth stop surface on the harvester, the depth stop surface configured to maintain a constant depth of cut into the native tendon for a range of harvester elevation angles relative to a guide longitudinal axis.

4. The tendon harvesting system of claim 3 wherein both of the curved leading edges extend along at least a 90 degree arc.

5. The tendon harvesting system of claim 3 wherein the range of elevation angles ranges between 0-80 degrees relative to the guide longitudinal axis.

6. The tendon harvesting system of claim 1 wherein the guide first end defines an entrance aperture, configured to receive the first and second blades therethrough.

7. The tendon harvesting system of claim 1 wherein the harvester includes a translation stop surface configured to engage a surface of the guide and limit translation of the harvester along the native tendon and towards the guide second end and thereby limit a length of the two lateral sides of the graft.

8. The tendon harvesting system of claim 7 wherein the harvester translation stop surface is axially spaced from the first and second blade and the handle, disposed between the first and second blade and the handle.

9. The tendon harvesting system of claim 7 wherein the harvester translation stop surface is configured to engage two legs of the guide to limit translation of the harvester towards the guide second end.

10. The tendon harvesting system of claim 1 wherein the guide includes a pair of legs configured to extend in a direction generally away from the native tendon anterior surface, the pair of legs configured to engage a stop surface of the harvester and define a translation limit of the first and second blades along the native tendon.

11. The tendon harvesting system of claim 1 wherein the guide elongate body is anteriorly spaced to allow for observation of the native tendon anterior surface.

12. The tendon harvesting system of claim 1 wherein the harvester is configured to operatively engage the guide to direct a trajectory of the harvester along the native tendon.

\* \* \* \* \*